United States Patent
Amini et al.

(10) Patent No.: US 10,676,794 B2
(45) Date of Patent: *Jun. 9, 2020

(54) DETECTION OF MICROORGANISMS IN FOOD SAMPLES AND FOOD PROCESSING FACILITIES

(71) Applicant: Clear Labs, Inc., Menlo Park, CA (US)

(72) Inventors: Sasan Amini, Redwood City, CA (US); Ramin Khaksar, Redwood City, CA (US); Michael Taylor, Kensington, MD (US); Hossein Namazi, Menlo Park, CA (US); David Tran, Santa Rosa, CA (US); Christopher Haney, Mountain View, CA (US); Pavan Vaidyanathan, Palo Alto, CA (US); Sima Mortazavi, Foster City, CA (US); Adam Allred, Menlo Park, CA (US)

(73) Assignee: Clear Labs, Inc., Menlo Park, CA (US)

( * ) Notice: Subject to any disclaimer, the term of this patent is extended or adjusted under 35 U.S.C. 154(b) by 202 days.

This patent is subject to a terminal disclaimer.

(21) Appl. No.: 16/054,682

(22) Filed: Aug. 3, 2018

(65) Prior Publication Data
US 2019/0204317 A1    Jul. 4, 2019

Related U.S. Application Data

(62) Division of application No. 15/927,913, filed on Mar. 21, 2018, now Pat. No. 10,101,328.
(Continued)

(51) Int. Cl.
*C12Q 1/68*    (2018.01)
*C12Q 1/689*   (2018.01)
(Continued)

(52) U.S. Cl.
CPC ......... *C12Q 1/689* (2013.01); *C12N 15/1065* (2013.01); *C12Q 1/10* (2013.01);
(Continued)

(58) Field of Classification Search
None
See application file for complete search history.

(56) References Cited

U.S. PATENT DOCUMENTS 8,124,355 B2   2/2012   Miller
8,840,848 B2   9/2014   Kraihanzel
(Continued)

FOREIGN PATENT DOCUMENTS

WO   WO-2012024658 A2   2/2012
WO   WO-2014039963 A1   3/2014
(Continued)

OTHER PUBLICATIONS

Quick et al., Rapid draft sequencing and real-time nanopore sequencing in a hospital outbreak of *Salmonella*, Genome Biol. May 30, 2015;16:114.*
(Continued)

*Primary Examiner* — Aaron A Priest
(74) *Attorney, Agent, or Firm* — Wilson Sonsini Goodrich & Rosati

(57) ABSTRACT

Provided herein are methods and apparatus for the identification of pathogenic and non-pathogenic microorganisms in food and environmental samples. The disclosure solves existing challenges encountered in identifying food borne pathogens, including pathogens of the *Salmonella, Campylobacter, Listeria*, and *Escherichia* genera in a timely and efficient manner. The disclosure also provides methods for differentiating a transient versus a resident pathogen, corre-
(Continued)

Generating blocks with pairwise Levenshtein distance as large as possible.

Periodic Block Design: Create barcodes by repeating each block multiple times, in the example figured below 3 times.

Nonperiodic Block Design: Create barcodes by concatenating multiple blocks that are unique to each barcode.

lating presence of non-pathogenic with pathogenic microorganisms, distinguishing live versus dead microorganisms by sequencing.

24 Claims, 24 Drawing Sheets

Related U.S. Application Data

(60) Provisional application No. 62/611,846, filed on Dec. 29, 2017.

(51) Int. Cl.
| | |
|---|---|
| *G01N 33/569* | (2006.01) |
| *C12Q 1/6869* | (2018.01) |
| *C12N 15/10* | (2006.01) |
| *G16B 40/00* | (2019.01) |
| *G16B 30/00* | (2019.01) |
| *G16B 50/00* | (2019.01) |
| *C12Q 1/10* | (2006.01) |
| *G01N 33/02* | (2006.01) |
| *G01N 33/08* | (2006.01) |
| *G01N 33/12* | (2006.01) |
| *G16B 20/20* | (2019.01) |
| *G16B 50/30* | (2019.01) |

(52) U.S. Cl.
CPC ........... *C12Q 1/6869* (2013.01); *G01N 33/02* (2013.01); *G01N 33/08* (2013.01); *G01N 33/12* (2013.01); *G01N 33/56916* (2013.01); *G01N 33/56922* (2013.01); *G16B 30/00* (2019.02); *G16B 40/00* (2019.02); *G16B 50/00* (2019.02); *C12Q 2535/122* (2013.01); *C12Q 2563/116* (2013.01); *C12Q 2565/631* (2013.01); *C12Q 2600/154* (2013.01); *G16B 20/20* (2019.02); *G16B 50/30* (2019.02); *Y02A 50/451* (2018.01)

(56) References Cited

U.S. PATENT DOCUMENTS

| | | | |
|---|---|---|---|
| 9,034,597 | B2 | 5/2015 | Bitinaite et al. |
| 10,101,328 | B1 | 10/2018 | Amini et al. |
| 10,246,704 | B1 | 4/2019 | Amini et al. |
| 2012/0040343 | A1 | 2/2012 | Timp et al. |
| 2014/0161686 | A1 | 6/2014 | Bort et al. |
| 2015/0176064 | A1 | 6/2015 | Fach et al. |
| 2015/0294065 | A1 | 10/2015 | Gautier et al. |
| 2015/0322426 | A1 | 11/2015 | Zografos et al. |
| 2016/0239732 | A1* | 8/2016 | Amini ................. C12Q 1/6874 |
| 2016/0257984 | A1 | 9/2016 | Hardenbol et al. |
| 2017/0044598 | A1 | 2/2017 | Armes et al. |
| 2017/0113216 | A1 | 4/2017 | Amini et al. |

FOREIGN PATENT DOCUMENTS

| | | |
|---|---|---|
| WO | WO-2016179190 A1 | 11/2016 |
| WO | WO-2016196942 A1 | 12/2016 |
| WO | WO-2017106542 A1 | 6/2017 |
| WO | WO-2017165269 A1 | 9/2017 |

OTHER PUBLICATIONS

Juul et al., What's in my pot? Real-time species identification on the MinION, bioRxiv 030742; doi: https://doi.org/10.1101/030742, Nov. 6, 2015.*

Mitsuhashi et al., A portable system for rapid bacterial composition analysis using a nanopore-based sequencer and laptop computer, Sci Rep. Jul. 18, 2017;7(1):5657.*

Hyeon et al., Quasimetagenomics-Based and Real-Time-Sequencing-Aided Detection and Subtyping of *Salmonella enterica* from Food Samples, Appl Environ Microbiol. Feb. 15, 2018; 84(4): e02340-17, Prepublished online Dec. 1, 2017.*

Greninger et al., Rapid metagenomic identification of viral pathogens in clinical samples by real-time nanopore sequencing analysis, Genome Med. Sep. 29, 2015;7:99.*

UMass, Indexing and Barcoding for Illumina NextGen Sequencing, available at https://www.umassmed.edu/contentassets/5ea3699998c442bb8c9b1a3cf95dbb24/indexing-and-barcoding-for-illumina-nextgen-sequencing.pdf, accessed Jul. 31, 2018.*

Biomerieux Vidas, Available at www.biomerieux-usa.com/phage, Accessed on Nov. 21, 2017.

Cardinali, et al. Next Generation Sequencing: problems and opportunities for next generation studies of microbial communities in food and food industry. Current Opinion in Food Science. 2017, 17:62-67.

Co-pending U.S. Appl. No. 15/927,913, filed Mar. 21, 2018.

Co-pending U.S. Appl. No. 15/927,958, filed Mar. 21, 2018.

Co-pending U.S. Appl. No. 15/928,023, filed Mar. 21, 2018.

Crowley, et al., Evaluation of VIDAS *Salmonella* (SLM) easy *Salmonella* method for the detection of *Salmonella* in a variety of foods: collaborative study, J. AOAC Int. Nov.-Dec. 2011; 94(6):1821-34.

Greninger, et al., Rapid metagenomic identification of viral pathogens in clinical samples by real-time nanopore sequencing analysis, Genome Medicine, (2015) 7:99, 13 pages.

Jain et al., The Oxford Nanopore MinION: delivery of nanopore sequencing to the genomics community, Genome Biology, (2016) 17:239, 11 pages.

Juul, et al., What's in my pot? Real-time species identification on the MinIONTM, first posted online Nov. 6, 2015, 9 pages.

Kerkhof, et al., Profiling bacterial communities by MinION sequencing of ribosomal operons, Microbiome (2017) 5:116, 11 pages.

Masser et al. Targeted DNA Methylation Analysis by Next-generation Sequencing, J Vis. Exp. (96):52488 (2015).

Mitsuhashi, et al., A portable system for metagenomic analyses using nanopore-based sequencer and laptop computers can realize rapid on-site determination of bacterial compositions, biorxiv, first posted online, Jan. 20, 2017, 36 pages.

Pincus, Microbial Identification Using the Biomérieux Vitek® 2 System, Available at https://store.pda.org/tableofcontents/ermm_v2_ch01.pdf, Accessed on Nov. 21, 2017.

Quick, et al., Rapid draft sequencing and real-time nanopore sequencing in a hospital outbreak of *Salmonella*, Genome Biology, (2015) 16:114, 14 pages.

Smith, et al. Reading canonical and modified nucleotides in 16S ribosomal RNA using nanopore direct RNA sequencing. Preprint available Apr. 29, 2017 on bioRxiv at https://doi:https://doi.org/10.1101/132274; Year: 2017.

UMass, Indexing and Barcoding for Illumina NextGen Sequencing, available at https://www.umassmed.edu/contentassets/5ea3699998c442bb8c9b1a3cf95dbb24/indexing-and-barcoding-for-illunnina-nextgen-sequencing.pdf, accessed Jul. 31, 2018.

U.S. Appl. No. 15/927,913 Notice of Allowance dated Aug. 10, 2018.

U.S. Appl. No. 15/928,023 Office Action dated Jul. 20, 2018.

Ziller et al. Targeted bisulfite sequencing of the dynamic DNA methylome, Epigenetics & Chromatin 9:55 (2016).

U.S. Appl. No. 15/927,958 Office Action dated Oct. 5, 2018.

Tyler, et al. Evaluation of Oxford Nanopore's MinION Sequencing Device for Microbial Whole Genome Sequencing Applications. Sci Rep. 2018; 8: 10931. Published online Jul. 19, 2018. doi: 10.1038/s41598-018-29334-5.

Bio-Rad. iQ-Check® Listeria monocytogenes II PCR Detection Kit #3578124.Available at http://www.bio-rad.com/en-us/sku/3578124-iq-check-listeria-monocytogenes-ii-pcr-detection-kit?ID=3578124. Accessed Mar. 8, 2019.

Co-pending U.S. Appl. No. 16/262,747, filed Jan. 30, 2019 by Amini et al.

Corvium. Improve Food Safety and Quality with Our Risk Reducing Software; Our food safety software helps you to reduce your risk

(56) References Cited

OTHER PUBLICATIONS and protect your brand from food recalls. Available at: https://www.corvium.com. Accessed on Mar. 8, 2019.

Enviromap. Environmental monitoring has never been easier. Available at: https://digital-solutions.merieuxnutrisciences.com/en/content/enviromap. Accessed on Mar. 8, 2019.

GB1805548.3 Combined Search and Examination Report dated Dec. 11, 2018.

Hygiena. RiboPrinter System; Microbial Identification & Characterization. 2003; Rev 01. Available at: http://www.fcbiotech.com.tw/wp-content/uploads/2017/10/%E9%A3%9F%E5%93%81%E5%BE%AE%E7%94%9F%E7%89%A92.pdf. Accessed on Mar. 8, 2019.

Laszlo, et al. Detection and mapping of 5-methylcytosine and 5-hydroxymethylcytosine with nanopore MspA. Proc Natl Acad Sci U S A. Nov. 19, 2013;110(47):18904-9. doi: 10.1073/pnas.1310240110. Epub Oct. 28, 2013.

Nguyen, et al. Real-time demultiplexing Nanopore barcoded sequencing data with npBarcode. Bioinformatics. Dec. 15, 2017;33(24):3988-3990. doi: 10.1093/bioinformatics/btx537.

Nocker, et al. Selective detection of live bacteria combining propidium monoazide sample treatment with microarray technology. Journal of Microbiological Methods, 2009, 76(3):253-261.

PCT/US2018/067750 International Search Report and Written Opinion dated Mar. 8, 2019.

Hygiena. Bax® System X5 PCR Pathogen Detection. MPB-2002_Rev 02.

U.S. Appl. No. 15/927,958 Office Action dated Mar. 4, 2019.

U.S. Appl. No. 15/928,023 Notice of Allowance dated Dec. 18, 2018.

U.S. Appl. No. 15/928,023 Notice of Allowance dated Jan. 17, 2019.

U.S. Appl. No. 16/262,747 Office Action dated Apr. 12, 2019.

Wescoe, et al. Nanopores discriminate among five C5-cytosine variants in DNA. J Am Chem Soc. Nov. 26, 2014;136(47):16582-7. doi: 10.1021/ja508527b. Epub Nov. 14, 2014.

\* cited by examiner

|  | Manual | Automated | Manual | Automated | Manual | Automated | Manual | Automated | Manual | Automated |
|---|---|---|---|---|---|---|---|---|---|---|
| All Reads | 2196000 | 2213000 | 1945661 | 1961292 | 2342638 | 2467129 | 1267892 | 1305108 |
| Enteritidis | ✓ | ✓ | ✓ | ✓ | ✓ | ✓ | ✓ | ✓ |
| Thyphimurium | ✓ | ✓ | ✓ | ✓ | ✓ | ✓ | ✓ | ✓ |
| I 4_[5]_12:i:- | ✓ | ✓ | ✓ | ✓ | ✓ | ✓ | ✓ | ✓ |
| Newport | ✓ | ✓ | ✓ | ✓ | ✓ | ✓ | ✓ | ✓ |
| Javiana | ✓ | ✓ | ✓ | ✓ | ✓ | ✓ | ✓ | ✓ |
| Infantis | ✓ | ✓ | ✓ | ✓ | ✓ | ✓ | ✓ | ✓ |
| Montevideo | ✓ | ✓ | ✓ | ✓ | ✓ | ✓ | ✓ | ✓ |
| Heidelberg | ✓ | ✓ | ✓ | ✓ | ✓ | ✓ | ✓ | ✓ |
| Muenchen | ✓ | ✓ | ✓ | ✓ | ✓ | ✓ | ✓ | ✓ |
| Saintpaul | ✓ | ✓ | ✓ | ✓ | ✓ | ✓ | ✓ | ✓ |

*Fig. 20*

Generating blocks with pairwise Levenshtein distance as large as possible.

Periodic Block Design: Create barcodes by repeating each block multiple times. In the example figured below 3 times.

Nonperiodic Block Design: Create barcodes by concatenating multiple blocks that are unique to each barcode.

DETECTION OF MICROORGANISMS IN FOOD SAMPLES AND FOOD PROCESSING FACILITIES

CROSS-REFERENCE

This application is a divisional of U.S. patent application Ser. No. 15/927,913, filed Mar. 21, 2018, which claims priority to Provisional Patent Application Ser. No. 62/611,846, filed on Dec. 29, 2017, which is incorporated herein by reference in its entirety.

BACKGROUND

Food producers recall their products from the marketplace when the products are mislabeled or when the food may present a health hazard to consumers because the food is contaminated or has caused a foodborne illness outbreak. Although these producers rely on several existing monitoring programs for pathogens, natural toxins, pesticides, and other contaminants about 48 million cases of foodborne illness are still identified annually in the United States alone—the equivalent of sickening 1 in 6 Americans each year. And each year these illnesses result in an estimated 128,000 hospitalizations and 3,000 deaths. The threats are numerous and varied, with symptoms ranging from relatively mild discomfort to very serious, life-threatening illness. While the very young, the elderly, and persons with weakened immune systems are at greatest risk of serious consequences from most foodborne illnesses, some of the microorganisms detected in foods pose grave threats to all persons.

SUMMARY

In some aspects the disclosure provides a method comprising: (a) deploying an assay to one or more food processing facilities; (b) performing a sequencing reaction of a food sample or of an environmental sample from said one or more food processing facilities; (c) transmitting an electronic communication comprising a data set associated with said sequencing reaction of said food sample or of said environmental sample from said one or more food processing facilities to a server; and (d) scanning, by a computer, at least a fraction of said transmitted data set for one or more polymorphic regions associated with a microorganism.

In some instances, said scanning scans fewer than 1% of said transmitted data set for one or more genes associated with said microorganism. In some instances, said sequencing reaction is a pore sequencing reaction. Said pore sequencing reaction can distinguish an epigenetic pattern on a nucleic acid from said food sample or from said environmental sample, such as a methylation pattern. In some instances, said microorganism is pre-selected by a customer. In some instances, the method further comprising scanning, by a computer, at least a fraction of said transmitted data set for one or more genes associated with two or more microorganisms. In some instances, said microorganism is selected from the group consisting of: a microorganism of the *Salmonella* genus, a microorganism of the *Campylobacter* genus, a microorganism of the *Listeria* genus, and a microorganism of the *Escherichia* genus. In some instances, said food sample is a perishable. In some instances, said perishable is a poultry, a red meat, a fish, a swine, a fruit, an egg, a vegetable, a produce, or a legume. In some instances, said environmental sample is a surface swab or a surface rinse of said one or more food processing facilities. In some instances, said environmental sample is a food storage container, a food handling equipment from said one or more food processing facilities, or a piece of clothing from a worker of said one or more food processing facilities. In some instances, the method further comprises amplifying or enriching one or more nucleic acids of said food sample or of said environmental sample prior to performing said sequencing reaction. In some instances, the method further comprises adding at least one barcode to one or more nucleic acids of said food sample or of said environmental sample prior to performing said sequencing reaction. In some instances, the method further comprises creating, in a computer, a data file that associates said at least one barcode with a source of said food sample or of said environmental sample. In some instances, said scanning comprises scanning said transmitted data set for one or more polymorphic gene regions. In some instances, said one or more polymorphic regions comprise one or more single nucleotide polymorphisms (SNP's), one or more restriction fragment length polymorphisms (RFLP's), one or more short tandem repeats (STRs), one or more variable number of tandem repeats (VNTR's), one or more hypervariable regions, one or more minisatellites, one or more dinucleotide repeats, one or more trinucleotide repeats, one or more tetranucleotide repeats, one or more simple sequence repeats, one or more indel, or one or more insertion elements. In some instances, said sequencing reaction differentiates a live microorganism from a dead microorganism. In other instances, said sequencing reaction differentiates a resident microorganism as compared to a transient microorganism. In some instances, said method distinguishes a microorganism from an *Escherichia* genus from a microorganism of a *Citrobacter* genus or a Shiga-Toxin producing *E. coli* (STEC) from a non-STEC *E. coli*.

In some aspects, the disclosure provides a nucleic acid sequencing apparatus comprising: (a) a nucleic acid library preparation compartment comprising two or more chambers configured to prepare a plurality of nucleic acids from a sample for a sequencing reaction, wherein said compartment is operatively connected to a nucleic acid sequencing chamber; (b) a nucleic acid sequencing chamber, wherein said nucleic acid sequencing chamber comprises: (i) one or more flow cells comprising a plurality of pores or sequencing cartridges configured for the passage of a nucleic acid strand, wherein two or more of the one or more flow cells are juxtaposed to one another; and (c) an automated platform, wherein said automated platform is programmed to robotically move a sample from said nucleic acid library preparation compartment into said nucleic acid sequencing chamber. In some instances, said automated platform moves a second sample from said nucleic acid library preparation compartment or from previously failed sequencing chamber into said nucleic acid sequencing chamber upon detecting a failure or a completion of a sequencing reaction. In some instances, the sequencing apparatus adds a barcode to a plurality of nucleic acids in said two or more chambers of (a), thereby providing a plurality of barcoded nucleic acids for said sequencing reaction. In some instances, mutually exclusive barcodes are added to a plurality of nucleic acids in said two or more chambers of (a), thereby providing a plurality of mutually exclusive barcoded nucleic acids. In some aspects, said automated platform robotically moves two or more of said mutually exclusive barcoded nucleic acids into said nucleic acid sequencing chamber. In some instances, said automated platform robotically moves two or more of said mutually exclusive barcoded nucleic acids into a same flow cell of said one or more flow cells. In some instances, said sample is a food or an environmental sample. In some instances, said sample is a non-food sample, such as blood, plasma, urine, tissue, faces, bone marrow, saliva or cerebrospinal fluid.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 20: illustrates the performance of the disclosed automated handling system on samples spiked with 10 different *Salmonella* serotypes (*Enteritidis, Thyphimurium, I 4_[5]_12:i:, Newport, Javiana, Infantis, Montevideo, Heidelberg, Muenchen*).

DETAILED DESCRIPTION

Figure 1:
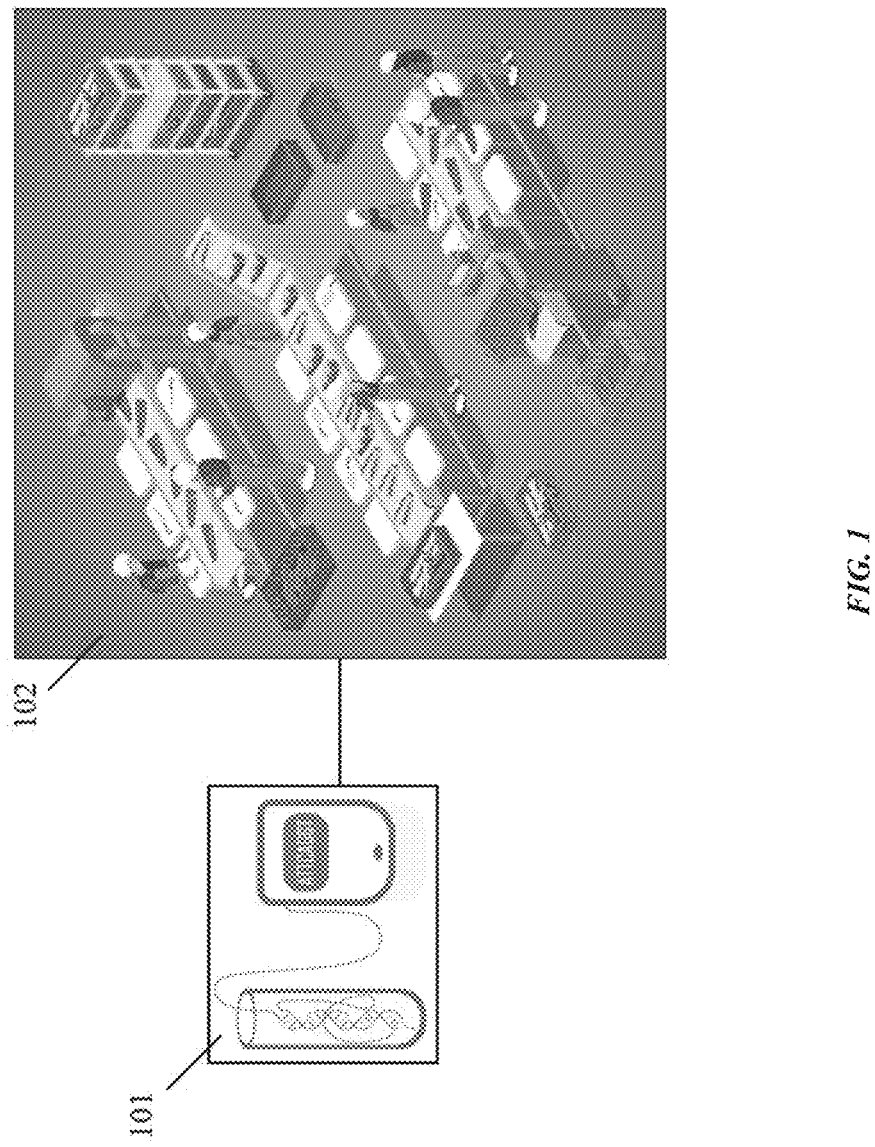
FIG. 1: illustrates the deploying of a sequencing assay 101 to one or more food processing facilities, food testing lab, or any other diagnostic lab 102 for performing a sequencing reaction of a food sample or of an environmental sample from said food processing facilities such as, for example, soil, water, air, animal product(s), feed, manure, crop production, or any sample associated with a manufacturing plant.

Food safety is a complex issue that has an impact on multiple segments of society. Usually a food is considered to be adulterated if it contains: (1) a poisonous or otherwise harmful substance that is not an inherent natural constituent of the food itself, in an amount that poses a reasonable possibility of injury to health, or (2) a substance that is an inherent natural constituent of the food itself; is not the result of environmental, agricultural, industrial, or other contamination; and is present in an amount that ordinarily renders the food injurious to health. The first includes, for example, a pathogenic bacterium, fungus, parasite or virus, if the amount present in the food may be injurious to health. An example of the second is the tetrodotoxin that occurs naturally in some organs of some types of pufferfish and that ordinarily will make the fish injurious to health. In either case, foods adulterated with these agents are generally deemed unfit for consumption.

Many different disease-causing microorganisms can contaminate foods, and there are many different foodborne infections. Although our scientific understanding of pathogenic microorganisms and their toxins is continually advancing, some of the most common microorganisms associated with foodborne illnesses include microorganisms of the *Salmonella, Campylobacter, Listeria,* and *Escherichia* genus.

*Salmonella* for example is widely dispersed in nature. It can colonize the intestinal tracts of vertebrates, including livestock, wildlife, domestic pets, and humans, and may also live in environments such as pond-water sediment. It is spread through the fecal-oral route and through contact with contaminated water. (Certain protozoa may act as a reservoir for the organism). It may, for example, contaminate poultry, red meats, farm-irrigation water (thereby contaminating produce in the field), soil and insects, factory equipment, hands, and kitchen surfaces and utensils.

*Campylobacter jejuni* is estimated to be the third leading bacterial cause of foodborne illness in the U.S. The symptoms this bacterium causes generally last from 2 to 10 days and, while the diarrhea (sometimes bloody), vomiting, and cramping are unpleasant, they usually go away by themselves in people who are otherwise healthy. Raw poultry, unpasteurized ("raw") milk and cheeses made from it, and contaminated water (for example, unchlorinated water, such as in streams and ponds) are major sources, but *C. jejuni* also occurs in other kinds of meats and has been found in seafood and vegetables.

Although the number of people infected by foodborne *Listeria* is comparatively small, this bacterium is one of the leading causes of death from foodborne illness. It can cause two forms of disease. One can range from mild to intense symptoms of nausea, vomiting, aches, fever, and, sometimes, diarrhea, and usually goes away by itself. The other, more deadly, form occurs when the infection spreads through the bloodstream to the nervous system (including the brain), resulting in meningitis and other potentially fatal problems.

*Escherichia* microorganisms are also diverse in nature. For instance, at least four groups of pathogenic *Escherichia coli* have been identified: a) Enterotoxigenic *Escherichia coli* (ETEC), b) Enteropathogenic *Escherichia coli* (EPEC), c) Enterohemorrhagic *Escherichia coli* (EHEC), and Enteroinvasive *Escherichia coli* (EIEC). While ETEC is generally associated with traveler's diarrhea some members of the EHEC group, such as *E. coli* O157:H7, can cause bloody diarrhea, blood-clotting problems, kidney failure, and death. Thus, it is important to be able not only to identify individual microorganism, but also to distinguish them.

Provided herein are methods and apparatus for the identification of pathogenic and non-pathogenic microorganisms in food and environmental samples. The disclosure solves existing challenges encountered in identifying food borne pathogens, including pathogens of the *Salmonella, Campylobacter, Listeria,* and *Escherichia* genus in a timely and efficient manner. The disclosure also provides methods for differentiating a transient versus a resident pathogen, correlating presence of non-pathogenic with pathogenic microorganisms, and distinguishing live versus dead microorganisms by sequencing, amongst others.

As used herein, the term "food processing facility" includes facilities that manufacture, process, pack, or hold food in any location globally. A food processing facility can, for example, determine the location and source of an outbreak of food-borne illness or a potential bioterrorism incident.

As used herein, the term "food" includes any nutritious substance that people or animals eat or drink, or that plants absorb, in order to maintain life and growth. Non-limiting examples of foods include red meat, poultry, fruits, vegetables, fish, pork, seafood, dairy products, eggs, egg shells, raw agricultural commodities for use as food or components of food, canned foods, frozen foods, bakery goods, snack food, candy (including chewing gum), dietary supplements and dietary ingredients, infant formula, beverages (including alcoholic beverages and bottled water), animal feeds and pet food, and live food animals. The term "environmental sample," as used herein, includes all food contact substances or items from a food processing facility. The term environmental sample includes a surface swab of a food contact substance, a surface rinse of a food contact substance, a food storage container, a food handling equipment, a piece of clothing from a subject in contact with a food processing facility, or another suitable sample from a food processing facility. The term "sample" as used herein, generally refers to any sample that can be informative of an environment or a food, such as a sample that comprises soil, water, water quality, air, animal production, feed, manure, crop production, manufacturing plants, environmental samples or food samples directly. The term "sample" may also refer to other non-food sample, such as samples derived from a subject, such as comprise blood, plasma, urine, tissue, faces, bone marrow, saliva or cerebrospinal fluid. Such samples may be derived from a hospital or a clinic.

As used herein, the term "subject," can refer to a human or to another animal. An animal can be a mouse, a rat, a guinea pig, a dog, a cat, a horse, a rabbit, and various other animals. A subject can be of any age, for example, a subject can be an infant, a toddler, a child, a pre-adolescent, an adolescent, an adult, or an elderly individual.

As used herein, the term "disease," generally refers to conditions associated with the presence of a microorganism in a food, e.g., outbreaks or incidents of foodborne disease.

The term "nucleic acid" or "polynucleotide," as used herein, refers to a polymeric form of nucleotides of any length, either ribonucleotides or deoxyribonucleotides. Polynucleotides include sequences of deoxyribonucleic acid (DNA), ribonucleic acid (RNA), or DNA copies of ribonucleic acid (cDNA).

The term "polyribonucleotide," as used herein, generally refers to polynucleotide polymers that comprise ribonucleic acids. The term also refers to polynucleotide polymers that comprise chemically modified ribonucleotides. A polyribonucleotide can be formed of D-ribose sugars, which can be found in nature, and L-ribose sugars, which are not found in nature.

The term "polypeptides," as used herein, generally refers to polymer chains comprised of amino acid residue monomers which are joined together through amide bonds (peptide bonds). The amino acids may be the L-optical isomer or the D-optical isomer.

The term "barcode," as used herein, generally refers to a label, or identifier, that conveys or is capable of conveying information about one or more nucleic acid sequences from a food sample or from an environmental sample associated with said food sample. A barcode can be part of a nucleic acid sequence. A barcode can be independent of a nucleic acid sequence. A barcode can be a tag attached to a nucleic acid molecule. A barcode can have a variety of different formats. For example, barcodes can include: polynucleotide barcodes; random nucleic acid and/or amino acid sequences; and synthetic nucleic acid and/or amino acid sequences. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads. Examples of such barcodes and uses thereof, as may be used with methods, apparatus and systems of the present disclosure, are provided in U.S. Patent Pub. No. 2016/0239732, which is entirely incorporated herein by reference. In some instances, as described herein, a "molecular index" can either be a barcode itself or it can be a building block, i.e., a component or portion of a larger barcode.

The term "sequencing," as used herein, generally refers to methods and technologies for determining the sequence of nucleotide bases in one or more nucleic acid polymers, i.e., polynucleotides. Sequencing can be performed by various systems currently available, such as, without limitation, a sequencing system by Illumina®, Pacific Biosciences (PacBio®), Oxford Nanopore®, Genia (Roche) or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw data corresponding to the genetic information associated with a food sample or an environmental sample. In some examples, such systems provide nucleic acid sequences (also "reads" or "sequencing reads" herein). The term also refers to epigenetics which is the study of heritable changes in gene function that do not involve changes in the DNA sequence. A read may include a string of nucleic acid bases corresponding to a sequence of a nucleic acid molecule that has been sequenced.

Analyzing Sequences Requested by a Customer

Many food poisoning outbreaks have been associated with pathogenic microorganisms including pathogens of the *Salmonella, Campylobacter, Listeria*, and *Escherichia* genus. Examples of foods that have been associated with such outbreaks include milk, cheeses, vegetables, meats (notably beef and poultry), fish, seafood, and many others. Potential contamination sources for various pathogens include raw materials, food workers, incoming air, water, and food processing environments. Among those, post-processing contamination at food-contact surfaces in a food processing facility poses a great threat to product contamination.

There are many challenges in ensuring the safety of our food supply. Some of these challenges include changes in a food processing environment that lead to food contamination, such as the introduction of a new lot of contaminated raw products. Other challenges include changes in food production and supply, which include importing and exporting foods from different jurisdictions, which may have distinct standards to assess a risk associated with a food. In addition, new and emerging bacteria strains, toxins, and antibiotic resistance may not be detected by traditional serotyping or PCR methods of detection.

In some aspects, the disclosure provides a method for the identification of a microorganism associated with a food or with a food processing facility. In some aspects the method comprises deploying an assay to one or more food processing facilities; performing a sequencing reaction of a food sample or of an environmental sample from said one or more food processing facilities; transmitting an electronic communication comprising a data set associated with said sequencing reaction of said food sample or of said environmental sample from said one or more food processing facilities to a server; and scanning, by a computer, at least a fraction of said transmitted data set for one or more genes associated with a microorganism.

In some instances, the scanning scans fewer than 1%, fewer than 0.1%, fewer than 0.001% of said transmitted data set for one or more genes associated with said microorganism. Said scanning can be performed to identify a variety of polymorphic gene regions (comprising SNP's, RFLP's, STRs, VNTR's, hypervariable regions, minisatellites, dinucleotide repeats, trinucleotide repeats, tetranucleotide repeats, simple sequence repeats, indels, and insertion elements) associated with a wide diversity of microorganisms. The variety of polymorphic regions to be searched for can be determined by creating a large database of sequences from dozens, hundreds and thousands of food and environmental samples. For instance, a database of such polymorphic regions can be constructed by performing sequencing reactions on at least 5,000, at least 10,000, at least 15,000, at least 20,000, at least 25,000, at least 30,000, at least 35,000, at least 40,000, at least 45,000, at least 50,000 different food or environmental samples. The sequences obtained can be used to compile information in a database that includes: a) the composition of each sample; and b) the presence or absence of a variety of pathogenic and non-pathogenic organisms associated on each sample. In addition to containing information about various types of genus and species, such databases comprise data from polymorphic gene regions of a variety of strains that are variants of a single species. For example, a plurality of sequences in the database might correspond to one or more serovars, morphovars, biovars, or other strain specific information.

A variety of sequencing techniques, such as a pore sequencing reaction, a next generation sequencing reaction, a shotgun next generation sequencing, or Sanger sequencing can be used to create a collection of polymorphic regions. In some instances, said sequencing reaction is a pore sequencing reaction and said pore sequencing reaction distinguishes an epigenetic pattern on a nucleic acid from said food sample or from said environmental sample.

In some cases, said microorganism may be pre-selected by a customer. A customer can be an individual or an entity, such as one or more food processing facilities. For example, a customer can be a food packaging facility; a food distribution center; a food storage center; a facilities handling meat, poultry, egg, or another edible product; a farm; a retail food establishment; a fishing vessel; or another type of facility that also manufactures, processes, packs, or holds foods for any period of time.

A customer may pre-select a microorganism of interest to be identified with any of the methods disclosed herein. For example, raw or undercooked ground beef and beef products are vehicles often implicated in *E. coli* O157:H7 outbreaks. Produce, including bagged lettuce, spinach, and alfalfa sprouts, are also increasingly being implicated in *E. coli* O157:H7 outbreaks. A food processing facility producing raw meats or other produce associated with *E. coli* O157:H7 may be a customer that pre-selects *E. coli* as a microorganism for analysis. A customer may pre-select one or more types of microorganisms for analysis. A microorganism can be one or more of types of bacteria, fungus, parasites, protozoa, and viruses.

Non-limiting examples of bacteria that can be pre-selected by a customer and detected with the methods of the disclosure include: bacteria in the *Escherichia* genus, including enterotoxigenic *Escherichia coli* (ETEC), enteropathogenic *Escherichia coli* (EPEC), enterohemorrhagic *Escherichia coli* (EHEC), and enteroinvasive *Escherichia coli* (EIEC); bacteria of the *Salmonella* genus; bacteria of the *Campylobacter* genus; bacteria of the *Listeria* genus; bacteria of the *Yersinia* genus; bacteria of the *Shigella* genus; bacteria of the *Vibrio* genus; bacteria of the *Coxiella* genus; bacteria of the *Mycobacterium* genus; bacteria of the *Brucella* genus; bacteria of the *Vibrio* genus; bacteria of the *Cronobacter* genus; bacteria of the *Aeromonas* genus; bacteria of the *Plesiomonas* genus; bacteria of the *Clostridium* genus; bacteria of the *Staphylococcus* genus; bacteria of the *Bacillus* genus; bacteria of the *Streptococcus* genus; bacteria of the *Clostridium* genus; and bacteria of the *Enterococcus* genus.

A microorganism can be a virus. Non-limiting examples of viruses that can be pre-selected by a customer and detected with the methods of the disclosure include: noroviruses, Hepatitis A virus, Hepatitis E virus, rotavirus.

The performing of a sequencing reaction of a food sample or of an environmental sample from said one or more food processing facilities often generates a plurality of nucleic acids sequences that contain redundant information or information associated with genes that are not from a microorganism. In some aspects, the disclosed methods empower efficient data analysis by facilitating the targeted analysis of a smaller data set. The generated data could be in the range of Kb, Mb, Gb, Tb or more per analyzed sample. In some aspects, said scanning scans fewer than 1/10, fewer than 1/20, fewer than 1/30, fewer than 1/40, fewer than 1/50, fewer than 1/60, fewer than 1/70, fewer than 1/80, fewer than 1/90, fewer than 1/100, fewer than 1/200, fewer than 1/300, fewer than 1/400, fewer than 1/500, fewer than 1/600, fewer than 1/700, fewer than 1/800, fewer than 1/900, fewer than 1/1,000, fewer than 1/10,000, or fewer than 1/100,000 of a data set, such as a transmitted data set for one or more genes associated with a microorganism. In some aspects, said scanning scans at least a fraction of said transmitted data set for one or more genes associated with two or more, three or more, four or more, five or more, six or more, seven or more, eight or more, nine or more, ten or more microorganisms or another suitable number. In some instances, said scanning comprises scanning said transmitted data set for one or more polymorphic gene regions. In some instances, said one or more polymorphic regions comprise one or more single nucleotide polymorphisms (SNP's), one or more restriction fragment length polymorphisms (RFLP's), one or more short tandem repeats (STRs), one or more variable number of tandem repeats (VNTR's), one or more hypervariable regions, one or more minisatellites, one or more dinucleotide repeats, one or more trinucleotide repeats, one or more tetranucleotide repeats, one or more simple sequence repeats, one or more indel, or one or more insertion elements. In some instances said one or more polymorphic regions comprise one or more single nucleotide polymorphisms (SNP's). A data set associated with a sequencing reaction of a food sample or of an environmental sample can be transmitted to a server and scanned by a computer.

In some cases, a method can detect a microorganism selected from the group consisting of: a microorganism of the *Salmonella* genus, a microorganism of the *Campylobacter* genus, a microorganism of the *Listeria* genus, and a microorganism of the *Escherichia* genus. The detected microorganisms may be of any serotype and a scanning, by a computer, of one or more genes associated with a microorganism may detect a microorganism independently of its serotype.

In some cases, a sequencing reaction of a food sample, an environmental sample, or another sample is a pore sequencing reaction, such as an Oxford Nanopore® sequencing reaction. In some instances, at least one barcode is added to one or more nucleic acid polymers derived from a food sample, from an environmental sample, or from another sample prior to performing said sequencing reaction. In some instances, a plurality of mutually exclusive barcodes are added to a plurality of food processing facilities, thereby creating a barcode identifier that can be associated with each food processing facility. For instance, a barcoded sequencing read comprising sequences from a pathogenic microorganism can be associated with a food or processing facility. In some aspects, a method disclosed herein further comprises creating, in a computer, a data file that associates said at least one barcode with a source of said food sample, of said environmental sample, or of another sample.

Figure 2:
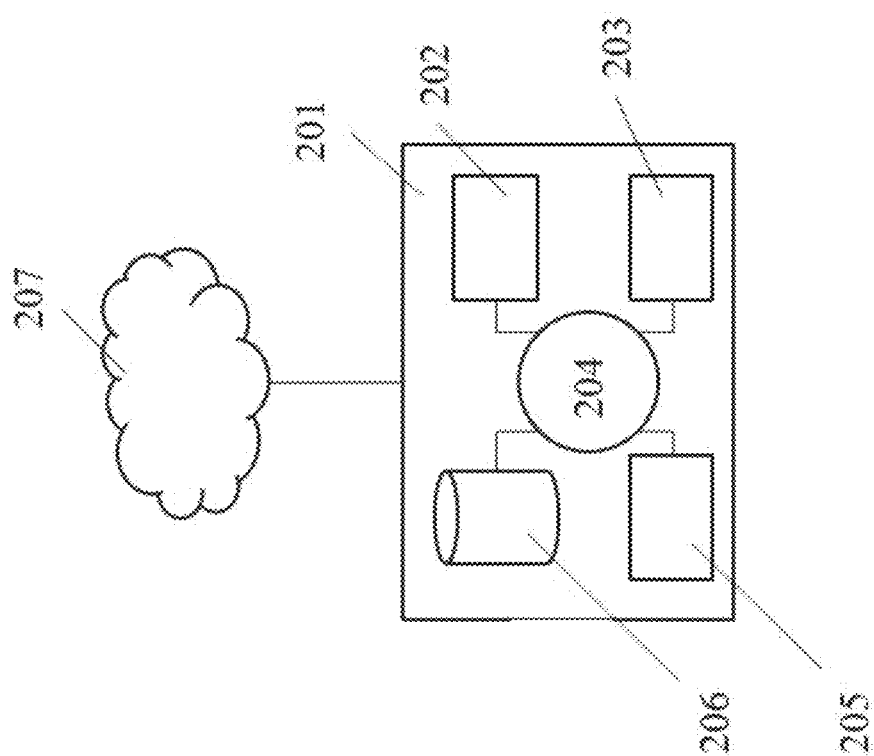
FIG. 2: illustrates a transmission of an electronic communication comprising a data set associated with a sequencing reaction from one or more food processing facilities to a server.

In some aspects, the disclosed methods comprise computer systems that are programmed to implement methods of the disclosure. FIG. 1 illustrates the deploying of a sequencing assay 101 to one or more food processing facilities 102, food testing lab, or any other diagnostic lab and performing a sequencing reaction of a food sample or of an environmental sample from said one or more food processing facilities 102. The food processing facility, food testing lab, or any other diagnostic lab may have one or more computer systems that can be used to transmit the results of the sequencing reads to a server, either on premise or remotely deployed cloud environment. FIG. 2 illustrates a transmission of an electronic communication comprising a data set associated with a sequencing reaction from one or more food processing facilities, food testing labs, or any other diagnostic labs to a server.

The raw sequence data collected from the sequencing reaction includes a large set of data that includes all individual sequences as well as the quality at each base. From this large data set, the Clear Labs bioinformatics pipeline extracts a final report that is orders of magnitudes smaller. The final report (e.g. electronic communication) is essentially limited to the presence or absence of an organism of interest, for instance pathogens, and a further classification of the organism in terms of serotypes, strains, or other subclassifications. The collected data not used in the report comprises the following:

(a) Read quality: The raw sequences include information on the quality of the sequences per base. The quality scores can be used in a Bayesian model where classifications are statistically sensitive to these quality scores. Furthermore the quality scores can reveal more on possible relations that content of samples have with the accuracy of sequencing platform.

(b) Sequence time: The raw sequences also include information on the time when the sequence was read by the sequencer. The number of sequences form the same source as a function of time can reveal a lot more information than we currently have. In addition, using these time data, can be useful in generating reports for all or some of the samples earlier than it is currently done.

(c) Trimmed portions of sequences: During demultiplexing of the sequences initial and terminal portions of those sequences are trimmed. Those portions include adapters, index barcodes, and primers. The main data extracted from the trimmed portions, identifies which sample the sequence belonged to. This decision however is influenced by sequencing errors, and special properties of the involved sequences. The information on accuracy of this decision, and other factors gets lost with trimming. Moreover the quality of these portions can be used as an indicator for the quality of the entire sequence.

(d) Clustering: An important step in the pipeline involves clustering sequences that are close enough to each other and representing all the sequences within a cluster by a consensus sequence. This reduces the data significantly and make is easier to classify these sequences. However these differences, even if minute, carry information that gets lost with clustering. Clustering with more stringent criteria, or no clustering can lead into higher resolution and perhaps finer classification.

A computer system 201 can be programmed or otherwise configured to process and transmit a data set from a food processing facility, food testing labs, or any other diagnostic labs. The computer system 201 includes a central processing unit (CPU, also "processor" and "computer processor" herein) 204, which can be a single core or multi core processor, or a plurality of processors for parallel processing. The computer system 201 also includes memory or memory location 205 (e.g., random-access memory, read-only memory, flash memory), electronic storage unit 206 (e.g., hard disk), communication interface 202 (e.g., network adapter) for communicating with one or more other systems, such as for instance transmitting a data set associated with said sequencing reads, and peripheral devices 204, such as cache, other memory, data storage and/or electronic display adapters. The memory 205, storage unit 206, interface 202 and peripheral devices 203 are in communication with the CPU 204 through a communication bus (solid lines), such as a motherboard. The storage unit 206 can be a data storage unit (or data repository) for storing data. For instance, in some cases, the data storage unit 206 can store a plurality of sequencing reads and provide a library of sequences associated with one or more strains from one or more microorganisms associated with a food processing facility, food testing labs, or any other diagnostic labs.

The computer system 201 can be operatively coupled to a computer network ("network") 207 with the aid of the communication interface 202. The network 207 can be the Internet, an internet and/or extranet, or an intranet and/or extranet that is in communication with the Internet. The network 207 in some cases is a telecommunication and/or data network. The network 207 can include one or more computer servers, which can enable distributed computing, such as cloud computing. The network 207, in some cases with the aid of the computer system 201, can implement a peer-to-peer network, which may enable devices coupled to the computer system 201 to behave as a client or a server.

High Sensitivity Detection of Microorganisms

Some families of microorganisms comprise both harmless and highly pathogenic bugs. The *Escherichia* family of pathogens, for example, comprise lethal and harmless strains of *E. coli*. Thus it is not only relevant to be able to identify a pathogen in a sample, but it is also relevant to be able to characterize it with high sensitivity. In some aspects, the disclosure provides a method comprising obtaining a plurality of nucleic acid sequences from a food sample, from an environment associated with said food sample or from another sample, such as non-food derived samples from clinical sources, including blood, plasma, urine, tissue, faces, bone marrow, saliva or cerebrospinal fluid samples; scanning, by a computer, at least a fraction of said plurality of said nucleic acid sequences for a plurality of nucleic acid regions from one or more microorganisms selected from the group consisting of: a microorganism of the *Salmonella* genus, a microorganism of the *Campylobacter* genus, a microorganism of the *Listeria* genus, and a microorganism of the *Escherichia* genus, wherein said scanning characterizes said one or more microorganisms with greater than 98% sensitivity, greater than 98.5% sensitivity, greater than 99% sensitivity, greater than 99.5% sensitivity, or greater than 99.9% sensitivity. In some aspects, said scanning characterizes said one or more microorganisms with greater than 98% specificity, greater than 98.5% specificity, greater than 99% specificity, greater than 99.5% specificity, or greater than 99.9% specificity. Sensitivity can be a measure of a microorganism that is correctly identified (e.g. the percentage of a microorganism that can be correctly identified based on sequencing read analyses). Specificity (also called the true negative rate) measures the proportion of negatives that are correctly identified as such (e.g. the percentage of food samples or environmental samples that are correctly identified as not having the microorganism therein). In some instances, said method can distinguish a genetic variant or subtype of a microorganism (e.g., one or more bacterial strains).

In some instances said plurality of nucleic acid sequences comprise complementary DNA (cDNA) sequences, ribonucleic acid (RNA) sequences, genomic deoxyribonucleic acid (gDNA) sequences or a mixture of cDNA, RNA, and gDNA sequences. In some instances, the high sensitivity of the disclosed method, the high specificity of the disclosed method, or both, can be accomplished by scanning said plurality of said nucleic acid sequences for one or more polymorphic gene regions associated with said microorganisms. In some instances, said one or more polymorphic regions is selected from the group consisting of one or more single nucleotide polymorphisms (SNP's), one or more restriction fragment length polymorphisms (RFLP's), one or more short tandem repeats (STRs), one or more variable number of tandem repeats (VNTR's), one or more hypervariable regions, one or more minisatellites, one or more dinucleotide repeats, one or more trinucleotide repeats, one or more tetranucleotide repeats, one or more simple sequence repeats, one or more indel, or one or more insertion elements. In some instances, said scanning compares a scanned polymorphism with a library of sequences comprising sequences from dozens, hundreds, or thousands of unique strains of a microorganism. The higher sensitivity is achieved by comparing the sequence information of the target region that can discriminate different microorganisms through the lens of SNPs, indels or other non-universal target specific markers that are only present within the genome of target micromicroorganisms.

Figure 3:
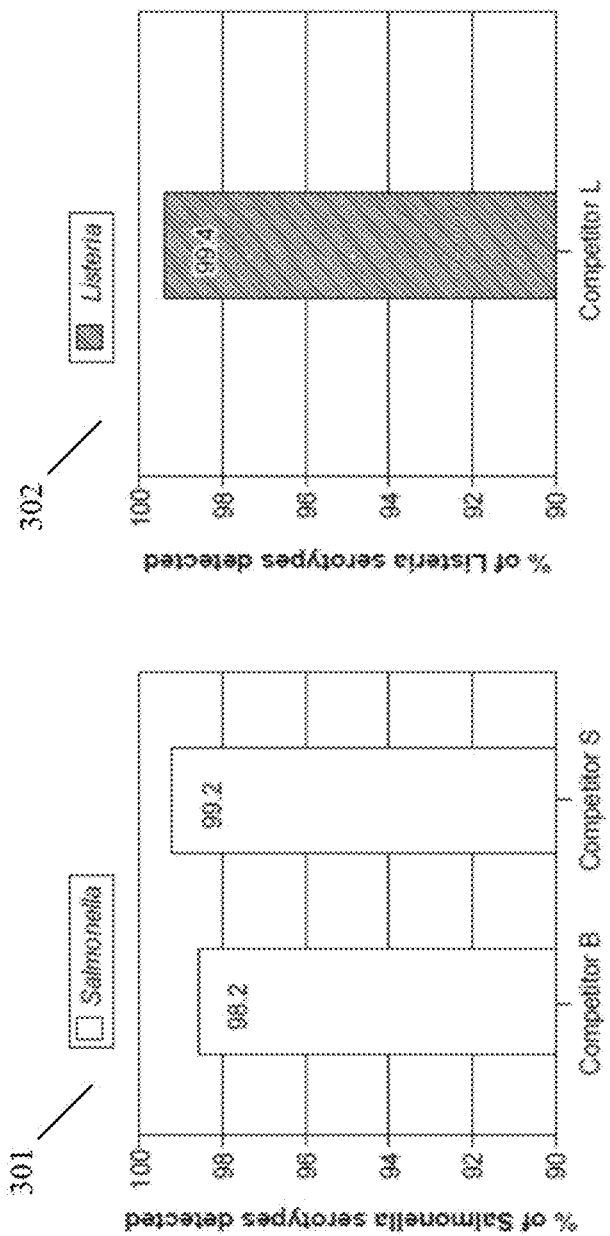
FIG. 3: is a chart illustrating that a redundancy in genetic markers decreases a false negative rate of a method of the disclosure.

In some aspects, an analysis of a redundancy in genetic markers increases a specificity and sensitivity of a method disclosed herein. FIG. 3 is a chart illustrating that a redundancy in genetic markers decreases a false negative rate of a method of the disclosure and increases its sensitivity as compared to PCR based methods. As shown in FIG. 3, three commercially available q/PCR based pathogen detection kits revealed that they would not detect all known *Salmonella* or *Listeria* genomes. 301 illustrates percentages of *Salmonella* detection by existing commercial kits. 302 illustrates percentages of *Listeria* detection by existing commercial kits.

A scanning of a plurality of nucleic acid regions within said plurality of nucleic acid sequences can characterize said one or more microorganisms with a desired specificity, sensitivity, or both. In some aspects, a scanning of no more than 0.001%, 0.01%, 0.1%, 1%, 5%, 10%, 25%, 50%, 90%, 99%, 100% or any number in between of nucleic acid regions within said plurality of nucleic acid sequences characterizes said one or more microorganisms with greater than 90%, 95%, 98%, 99%, 99.9%, 99.99% and 99.999% sensitivity. In some aspects, the method has fewer than 2%, fewer than 1.5%, fewer than 1.0%, fewer than 0.5%, or fewer than 0.1% of a false positive identification rate. In some aspects, a scanning of no more than 1% of a whole genome can characterize said microorganism.

In some instances, the high sensitivity and specificity of the disclosed methods are independent of a serotype of the microorganism. For instance, a scanning of a plurality of nucleic acid regions can identify a microorganism of the *Salmonella* genus that has a serotype selected from the group consisting of: *Enteritidis, Typhimurium, Newport, Javiana, Infantis, Montevideo, Heidelberg, Muenchen, Saintpaul, Oranienburg, Braenderup, Paratyphi B* var. *L*(+) *Tartrate+, Agona, Thompson*, and *Kentucky*; a microorganism of the *Escherichia* genus has a serotype selected from the group consisting of: O103, O111, O121, O145, O26, O45, and O157; a microorganism of the *Listeria* genus that has a serotype selected from the group consisting of: 2a, 1/2b, 1/2c, 3a, 3b, 3c, 4a, 4b, 4ab, 4c, 4d, and 4e; a microorganism of the *Campylobacter* genus with the *C. jejuni, C. lari,* or *E. coli* serotype and others.

A non-pathogenic strain of *Citrobacter*, namely *Citrobacter sedlakii*, expresses the *Escherichia coli* O157:H7 antigen. This is usually associated with a false positive detection of *E. coli* in a sample. Typically, when *Citrobacter* is erroneously classified as *E. coli*, a food lot may be unnecessarily disposed of and a food processing facility may be erroneously classified as a contaminated facility. In some aspects, the high sensitivity of the disclosed methods can be used to distinguish a microorganism from the *Escherichia* genus from a microorganism of the *Citrobacter* genus. In some instances, the disclosure provides a method comprising: scanning, by a computer, a plurality of sequencing reads from a food sample or from an environment associated with said food sample, whereby said scanning distinguishes a microorganism of a *Citrobacter* genus from a microorganism of an *Escherichia* genus by identifying one or more single nucleotide polymorphisms that are associated with either said *Citrobacter* genus or said *Escherichia* genus. Other examples include *E. coli* O157:H7 assay cross-reacting with *E. coli* O55 (which is not an STEC). Also some assays deliver false positives against *E. coli* O104 (which is not an STEC). *Citrobacter* is also a long-understood challenge for the some systems *E. coli* O157:H7.

Figure 4:
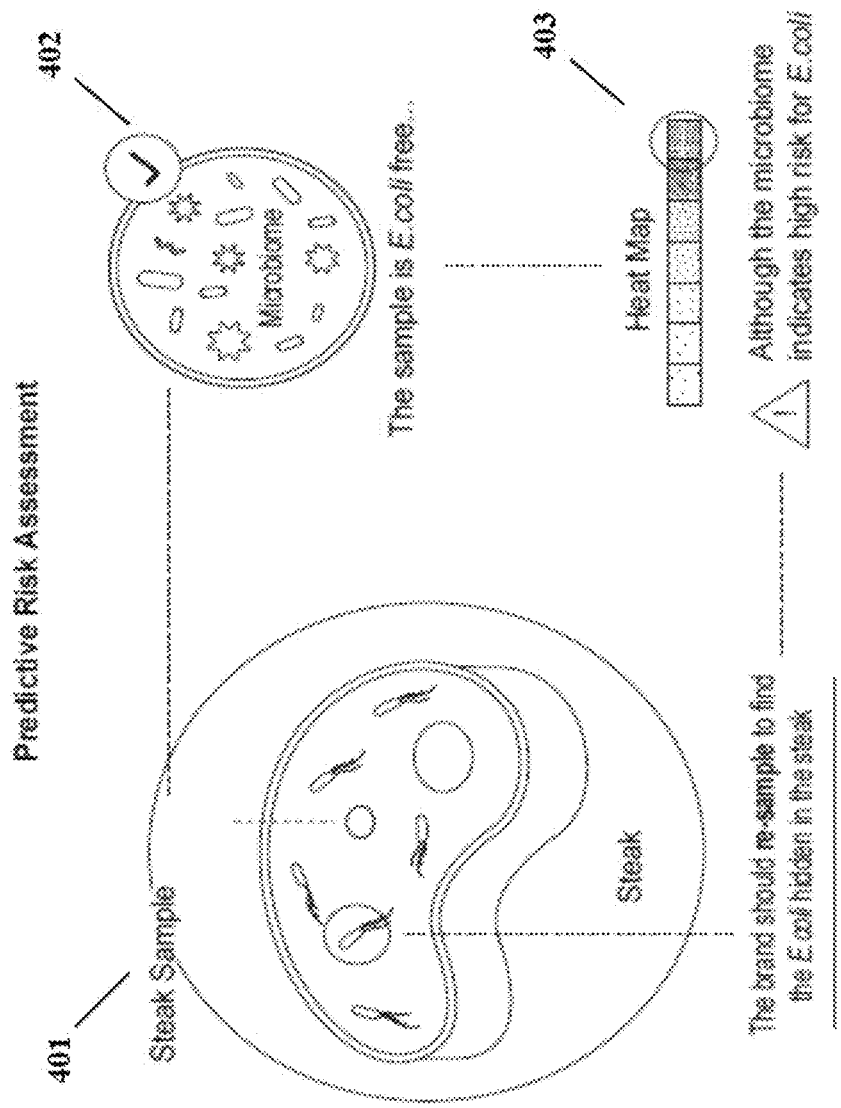
FIG. 4: illustrates a process for predictive risk assessment based on a detection of a non-pathogenic microorganism.

In many cases, disease outbreaks require a rapid response, often including multijurisdictional coordination. In some aspects, the disclosure provides methods for the rapid identification of a microorganism from a food sample. In some instances, the disclosure provides a method for sequencing a plurality of nucleic acid sequences from a food sample, from an environmental sample associated with said food sample or from another sample (such as a clinically derived sample) for a period of time; and performing an assay on said food sample or said environment associated with said food sample if said sequencing for said period of time identifies a threshold level of nucleic acid sequences from a microorganism in said food sample. In some instances said period of time is less than 12 hours, less than 6 hours, less than 4 hours, less than 2 hours, less than 1 hour, less than 30 minutes, less than 20 minutes, less than 15 minutes or another suitable time. FIG. 4 is a schematic illustrating a sequencing of a plurality of nucleic acid sequences from a food sample for a period of time and the advantages of performing an assay on said food sample if said sequencing for said period of time identifies a threshold level of nucleic acid sequences from a microorganism in said food sample.

Pathogenic Microorganisms

In general, a microorganism that can injure its host, e.g., by competing with it for metabolic resources, destroying its cells or tissues, or secreting toxins can be considered a pathogenic microorganism. Examples of classes of pathogenic microorganisms include viruses, bacteria, mycobacteria, fungi, protozoa, and some helminths. In some aspects, the disclosure provides methods for detecting one or more microorganisms from a food sample or from an environment associated with said food sample—such as from a table, a floor, a boot cover, an equipment of a food processing facility—or from a food related sample that comprise soil, water, water quality, air, animal production, feed, manure, crop production, manufacturing plants, environmental samples, or non-food derived samples, such as samples from clinical sources that comprise blood, plasma, urine, tissue, faces, bone marrow, saliva or cerebrospinal fluid by analyzing a plurality of nucleic acid sequencing reads from such samples.

Many pathogenic microorganisms are further subdivided into serotypes, which can differentiate strains by their surface and antigenic properties. For instance *Salmonella* species are commonly referred to by their serotype names. For example, *Salmonella enterica* subspecies *enterica* is further divided into numerous serotypes, including *S. enteritidis* and *S. typhimurium*. In some aspects, the methods of the disclosure can distinguish between such subspecies of a variety of *Salmonella* by analyzing their nucleic acid sequences.

*Escherichia coli* (*E. coli*) bacteria normally live in the intestines of people and animals. Many *E. coli* are harmless and in some aspects are an important part of a healthy human intestinal tract. However, many *E. coli* can cause illnesses, including diarrhea or illness outside of the intestinal tract and should be distinguished from less pathogenic strains. In some aspects, the methods of the disclosure can distinguish between various subspecies of a variety of *Escherichia* bacteria by analyzing their nucleic acid sequences.

*Listeria* is a harmful bacterium that can be found in refrigerated, ready-to-eat foods (meat, poultry, seafood, and dairy—unpasteurized milk and milk products or foods made with unpasteurized milk), and produce harvested from soil contaminated with, for example, *L. monocytogenes*. Many animals can carry this bacterium without appearing ill, which increases the challenges in identifying the pathogen derived from a food source. In addition, some species of *Listeria* can grow at refrigerator temperatures where most other foodborne bacteria do not, another factor that increases the challenges of identifying *Listeria*. When eaten, *Listeria* may cause listeriosis, an illness to which pregnant women and their unborn children are very susceptible. In some aspects, the methods of the disclosure can distinguish between various subspecies of a variety of *Listeria* bacteria by analyzing their nucleic acid sequences.

*Campylobacter jejuni* is estimated to be the third leading bacterial cause of foodborne illness in the United States. Raw poultry, unpasteurized ("raw") milk and cheeses made from it, and contaminated water (for example, unchlorinated water, such as in streams and ponds) are major sources of *Campylobacter*, but it also occurs in other kinds of meats and has been found in seafood and vegetables. In some aspects, the methods of the disclosure can distinguish between various subspecies of a variety of *Campylobacter* bacteria by analyzing their nucleic acid sequences.

Non-limiting examples of pathogenic microorganisms that can be detected with the methods of the disclosure include: pathogenic *Escherichia coli* group, including Enterotoxigenic *Escherichia coli* (ETEC), Enteropathogenic *Escherichia coli* (EPEC), Enterohemorrhagic *Escherichia coli* (EHEC), Enteroinvasive *Escherichia coli* (EIEC), *Salmonella* spp., *Campylobacter jejuni*, *Listeria*, *Yersinia enterocolitica*, *Shigella* spp., *Vibrio parahaemolyticus*, *Coxiella burnetii*, *Mycobacterium bovis*, *Brucella* spp., *Vibrio cholera*, *Vibrio vulnificus*, *Cronobacter*, *Aeromonas hydrophila* and other spp., *Plesiomonas shigelloides*, *Clostridium perfringens*, *Clostridium botulinum*, *Staphylococcus aureus*, *Bacillus cereus* and other *Bacillus* spp., *Listeria monocytogenes*, *Streptococcus* spp., *Enterococcus*, and others.

Identifying a New Microorganism in an Environment

Disclosed herein are methods and apparatuses that allow the distinction of a microorganism that has been newly introduced into a food processing facility or any other environmental setting in which tracking hygiene is critical, such as a hospital or a clinic. In some instances, resident microorganisms reflect a persistent contamination within a location, e.g., a food processing facility or a hospital, that is very different than the transient pathogens that are being repeatedly introduced into the locations. Discriminating resident and transient pathogens provides more clarity for differentiation of source of contaminations and intervention strategies. This strategy can be used, for example, to manage contaminations with managing contaminations with *Listeria monocytogensis*. For example, *Campylobacter* is part of the natural gut microflora of most food-producing animals, such as chickens, turkeys, swine, cattle, and sheep. Typically, each contaminated poultry carcass can carry from about 100 to about 100,000 *Campylobacter* cells. On one hand, given the fact that less than 500 *Campylobacter* cells can cause infection, poultry products pose a significant risk for consumers who mishandle fresh or processed poultry during preparation or who undercook it. On another hand, one must be able to distinguish a normal level of a *Campylobacter* on a food carcass from a *Campylobacter* overgrowth in a sample or from the presence of a new strain of *Campylobacter* in a food processing facility, environment, or food sample. One must also be able to identify a new source of contamination in a facility from existing sources. FIG. 4 illustrates a process for predictive risk assessment based on a detection of a non-pathogenic microorganism. Briefly, a food sample, such as a steak sample illustrated as 401 is processed and an assay, such as a nucleic acid sequencing reaction is performed. An analysis of a plurality of nucleic acid sequencing reads from 401 may, in some instances, not detect a particular pathogen, such as the *E. coli* pathogen illustrated in this example. Nevertheless, an analysis 403 of the microbiome 402 of the food sample 401 may indicate high risk for a presence of a pathogen, such as *E. coli*. In such instances, the food sample may be re-sampled and re-processed to confirm the presence of a pathogenic microorganism therein.

In some instances, the methods disclosed herein further comprise performing an additional assay to confirm the presence of the pathogenic microorganism in the sample, such as a serotyping assay, a polymerase chain reaction (PCR) assay, an enzyme-linked immunosorbent (ELISA) assay, or an enzyme-linked fluorescent assay (ELFA) assay, restriction fragment length polymorphisms (RFLP) assay, pulse field gel electrophoresis (PFGE) assay, multi-locus sequence typing (MLST) assay, targeted DNA sequencing assay, whole genome sequencing (WGS) assay, or shotgun sequencing assay.

In some aspects, the disclosure provides a method comprising obtaining a first plurality of nucleic acid sequences from a first sample of a food processing facility; creating a data file in a computer that associates one or more of said first plurality of nucleic acid sequences with said food processing facility; obtaining a second plurality of nucleic acid sequences from a second food sample of said food processing facility; and scanning a plurality of sequences from said second plurality of nucleic acid sequences for one or more sequences associated with said food processing facility in the created data file.

One or more data files can be created that associate a microorganism with a food processing facility. In some instances, a data file can provide a collection of sequencing reads that can be associated with one or more strains of a microorganism present in the processing facility. In some cases, more than 10, 15, 20, 25, 30, 35, 40, 45, 50, 60, 70, 80, 90, 100, or 1000 bacterial strains can be associated with one or more food processing facilities.

Figure 5:
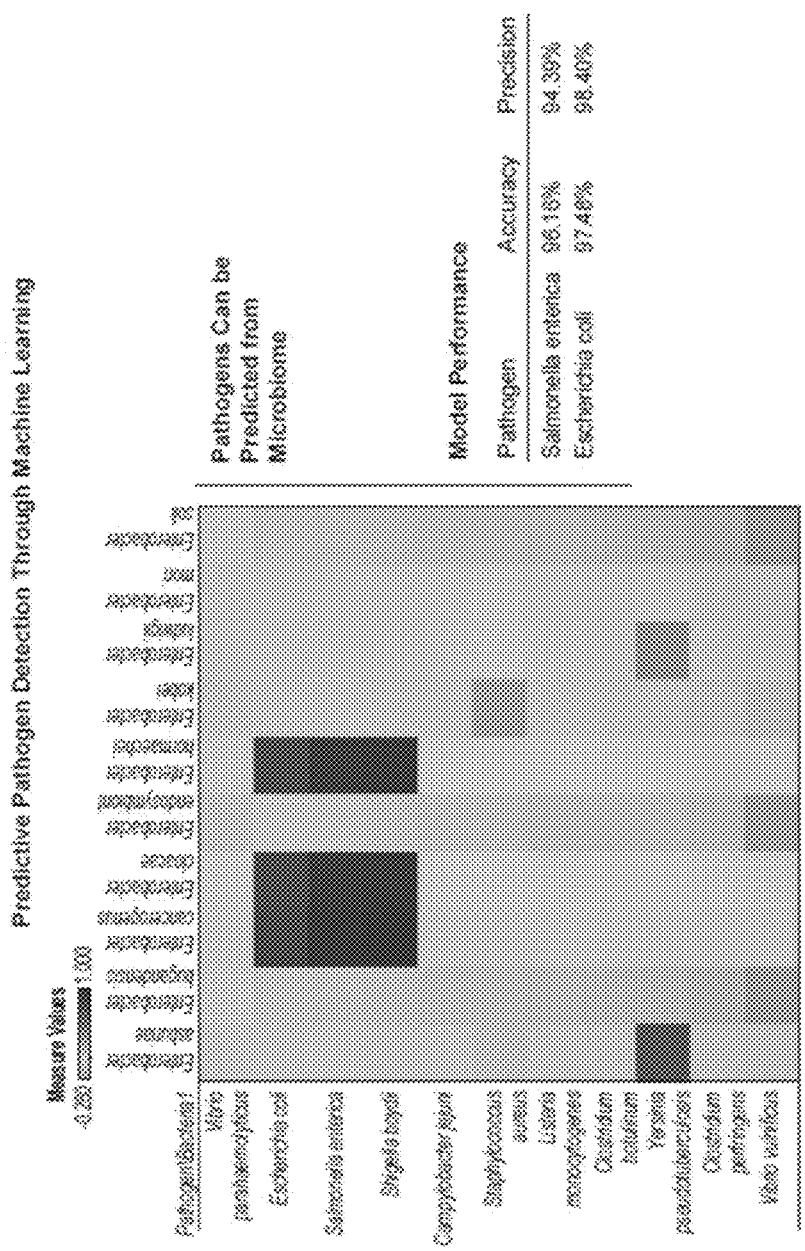
FIG. 5: is a heat map illustrating predictive pathogen detection through machine learning.

Correlating a Presence of a Microorganism with the Risk Associated with a Food Sample The instance disclosure recognizes that a presence of some non-pathogenic microorganisms, i.e. indicator microorganisms, can be correlated with a presence of pathogenic bacteria in food, in environmental samples, or another sample. In some aspects the disclosure provides a method comprising detecting a presence or an absence of a non-pathogenic microorganism in a food sample, an environment associated with said food sample, or another sample described herein, by a computer system, and a presence or an absence of a pathogenic microorganism in said food sample, environment associated, or another sample based on said presence or said absence of said non-pathogenic microorganism. FIG. 5 is a heat map illustrating predictive pathogen detection through machine learning using associated non-pathogenic microorganisms. Data was collected from more than 20,000 food samples varying over the food categories identified by CODEX, with presentation proportional to their market share. Among those about 950 samples were identified to have pathogens present. The pathogens were detected via Clear Labs sequencing platform, as well as, with traditional culturing. Via sequencing multiple regions, the bacteria present in the samples were detected and quantified (relative to each other) at the species level.

The data was supplemented by alpha diversity measures including Shannon entropy, number of observed OTUs, and Faith's phylogenetic diversity measure. The quantification of the bacteria in the samples and these supplemented measures, provided coordinates for the data points used in the final classification. The distance between the data points was computed as a combination of unifrac distance and the euclidean distance restricted to the supplemented coordinates.

The data points were split into training and test subsets. We used stratified 10-fold cross validation to train support vector machine model on the training set. The performance of the model was measured on the previously separated test set. The scores with regard to detection of some of the pathogens is presented in FIG. 5.

The coefficients of the support vector machine classifier were used to determine bacteria that play significance in determining presence or absence of the pathogens and therefore to provide signatures that can be used independently of the model. This analysis determined a set of non-pathogenic microorganisms that had statistically significant correlation with the presence of pathogenic organisms, including members of the genus *Enterobacter*. *Enterobacter asburiae*, *Enterobacter bugandensis*, *Enterobacter cancerogenus*, *Enterobacter cloacae*, *Enterobacter endosymbiont*, *Enterobacter hormaechei*, *Enterobacter kobei*, *Enterobacter ludwigii*, and *Enterobacter soli* were among the top 9 examples of non-pathogenic bacteria associated with our set of pathogenic bacteria. For example, *Yersinia pseudotuberculosis* was associated with *Enterobacter asburiae*; *Vibrio vulnificus* was associated with *Enterobacter bugandensis*, *Enterobacter endosymbiont*, and *Enterobacter soli*; *Escherichia coli*, *Salmonella enterica*, and *Shigella boydii* were associated with *Enterobacter cancerogenus*, *Enterobacter cloacae*, and *Enterobacter hormaechei*; *Staphylococcus Aureus* was associated with *Enterobacter kobei*; and *Yersinia pseudotuberculosis* was associated with *Enterobacter asburiae* and *Enterobacter ludwigii*.

Without being limited by theory, a variety of other samples described herein can be analyzed as described. Briefly, a sample may be screened with any one of the methods described herein and a plurality of nucleic acid sequences may be obtained. Numerous sequences within said plurality of nucleic acid sequences may be correlated by a machine learning algorithm with a variety of microorganisms. A prediction can then be created and a visual output of such prediction, such as the illustrated a heat map can be created by detecting statistically significant correlations. For instance, a heat map created by a machine learning algorithm may illustrate a correlation between a presence of *E. coli*, *Salmonella enterica*, and *Shigella boydii* of one or more non-pathogenic microorganisms from the *Enterobacter* genus, such as *Enterobacter cancerogenus*, *Enterobacter cloacae*, and *Enterobacter hormaechei* or any other bacterial genera. In some aspects, a machine learning algorithm, including the machine learning algorithm's described herein, can be used to create such predictions.

A statistical analysis can be performed to identify the top nonpathogenic species/food ingredients associated with the presence of *Vibrio/Staphylococcus/Yersinia/Shigella/Salmonella/Escherichia* (an illustrative cluster-based representation of such analysis is presented in FIG. 5). This analysis determined a set of non-pathogenic microorganisms that had statistically significant correlation with the presence of pathogenic organisms, including members of the genus *Enterobacter. Enterobacter asburiae, Enterobacter bugandensis, Enterobacter cancerogenus, Enterobacter cloacae, Enterobacter endosymbiont, Enterobacter hormaechei, Enterobacter kobei, Enterobacter ludwigii,* and *Enterobacter soli* were among the top 9 examples of non-pathogenic bacteria associated with our set of pathogenic bacteria. For example, *Yersinia pseudotuberculosis* was associated with *Enterobacter asburiae*; *Vibrio vulnificus* was associated with *Enterobacter bugandensis, Enterobacter endosymbiont*, and *Enterobacter soli*; *Escherichia coli, Salmonella enterica*, and *Shigella boydii* were associated with *Enterobacter cancerogenus, Enterobacter cloacae,* and *Enterobacter hormaechei*; *Staphylococcus Aureus* was associated with *Enterobacter kobei*; and *Yersinia pseudotuberculosis* was associated with *Enterobacter asburiae* and *Enterobacter ludwigii*.

Food is a chemically complex matrix. Predicting whether, or how fast, microorganisms will grow in a food, or how quickly a food may spoil, is difficult. For instance, most foods contain sufficient nutrients to support microbial growth. Furthermore, there are many additional factors that encourage, prevent, or limit growth of microorganisms in foods including pH, temperature, and relative humidity. In some aspects, the instant disclosure recognizes that a presence of some microorganism, whether or not pathogenic, can be correlated with a sell-by date, i.e., a spoilage date of a food. In some aspects the disclosure provides a method comprising: detecting a presence or an absence of a microorganism in a food sample or in an environmental sample from a food processing facility; and predicting, by a computer system, a risk presented by said food sample or by said food processing facility based on said presence or said absence of said microorganism.

Figure 6:
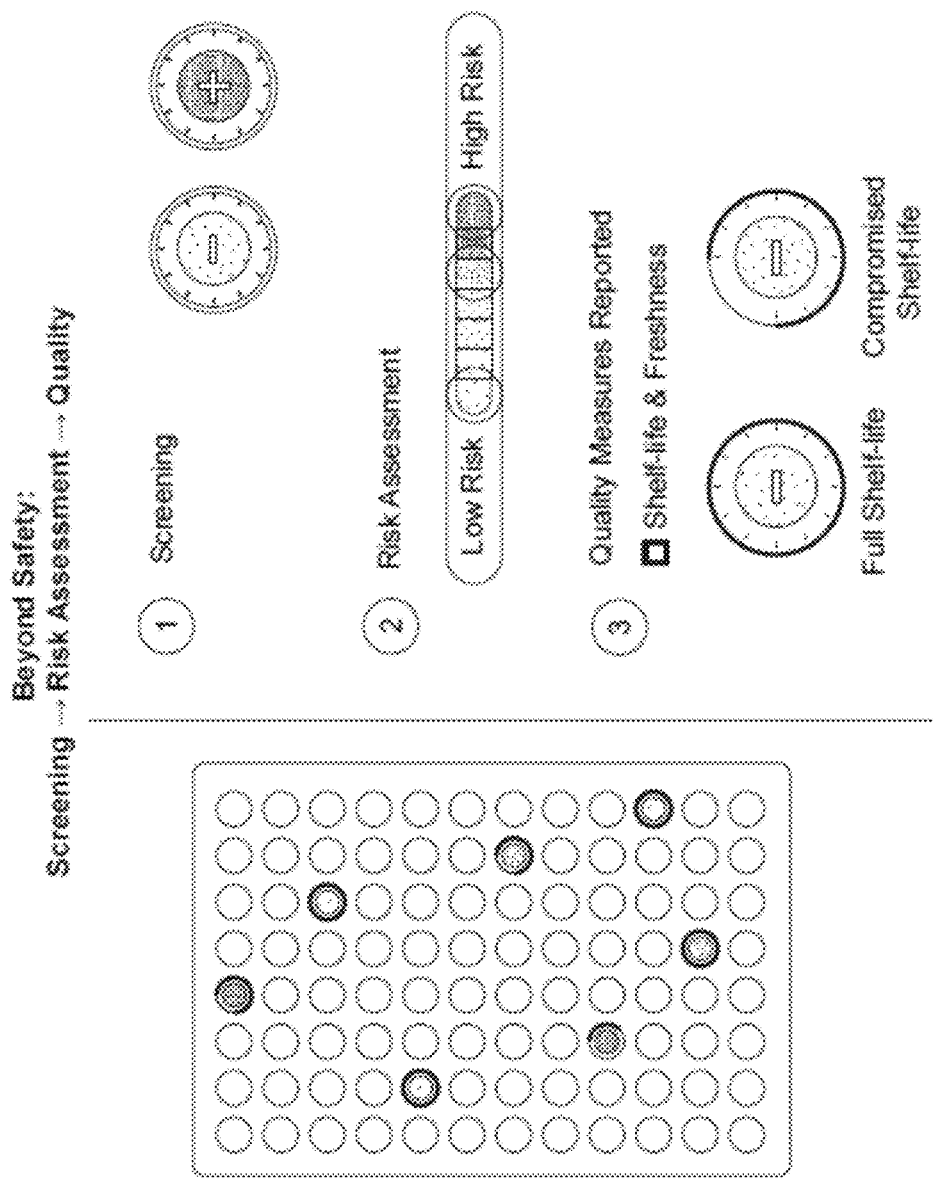
FIG. 6: illustrates a process for predicting a shelf-life of a food based on the detection of a microorganism.

FIG. 6 illustrates a process for predicting a shelf-life of a food based on machine learning. Briefly, FIG. 6 illustrates a screening of a sample, such as a screening of a plurality of nucleic acid sequencing reads. Subsequently, a machine learning algorithm is used to create a risk profile, whereby said risk profile associates a presence of some microorganism with a low or a high likelihood of food spoilage, thereby predicting the sell-by date of a food.

A machine learning algorithm can be used to associate any number of sequencing reads with a presence of microorganism in a food sample, a food related sample, or another sample. Similarly, a machine learning algorithm may be able to associate any number of sequencing reads with a presence of a pathogenic microorganism, even if the sequence reads themselves are not from the pathogenic microorganism. Computer-implemented methods for generating a machine learning-based classifier in a system may require a number of input datasets in order for the classifier to produce highly accurate predictions. Depending on the microorganism, matrix, and the microorganisms abundance in the real life samples of the matrix, the data can be in range of 100, 1000, 10000, 100000, 1000000, 10000000, 100000000 sequencing reads. A machine learning algorithm is selected from the group consisting of: a support vector machine (SVM), a Naïve Bayes classification, a random forest, Logistic regression and a neural network.

Tuning an Assay Resolution

Figure 7:
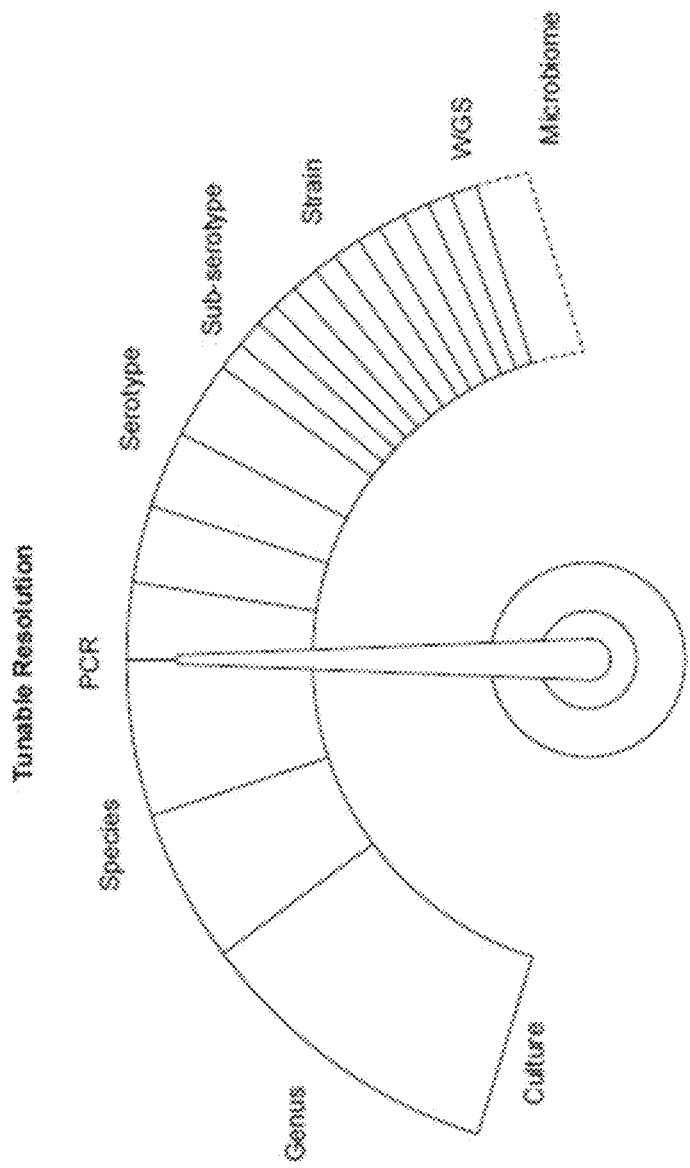
FIG. 7: is a diagram illustrating the tunable resolution of various assays.

One can tune the resolution for the detection of a microorganism based on the source of the sample, e.g., food versus surface swab; and the sensitivity of the assay itself, e.g., genus, species, serotype, versus strain (obtained via whole genome sequencing). FIG. 7 is a diagram illustrating the tunable resolution of various assays. Briefly, one or more assays can be used sequentially to obtain a desired level of sensitivity, such as to determine a genus, a species, a serotype, a sub-serotype, or a strain of said microorganism. The assays can be identical or they can be distinct. FIG. 7 illustrates that a sequencing assay can be used to identify a strain or a sub-serotype of a microorganism whereas a PCR reaction may be able to identify a species or, in some cases, a serotype of a particular microorganism.

In some aspects, the disclosure provides a method comprising: obtaining a plurality of nucleic acid sequences of a food sample, of an environmental sample or of another non-food derived sample from a food processing facility or another facility; performing a first assay in said plurality of nucleic acid sequences of said food sample, whereby said assay predicts a presence or predicts an absence of a microorganism in said food sample; and determining, based on said predicted presence or said predicted absence of said microorganism of the first assay whether to perform a second assay, whereby a sensitivity of said second assay is selected to determine a genus, a species, a serotype, a sub-serotype, or a strain of said microorganism.

There are various approaches for processing nucleic acids from food samples or from environmental samples, such as polymerase chain reaction (PCR) and sequencing. In some cases said assay is a sequencing assay that provides the ability to obtain sequencing-reads in real time, such as pore sequencing assay. Sequencing can be performed by various systems currently available, such as, without limitation, a sequencing system by Illumina®, Pacific Biosciences (PacBio®), Oxford Nanopore®, Genia (Roche) or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. In some cases, the assay is an enzyme-linked immunosorbent (ELISA) assay or an enzyme-linked fluorescent assay (ELFA) assay.

Figure 8:
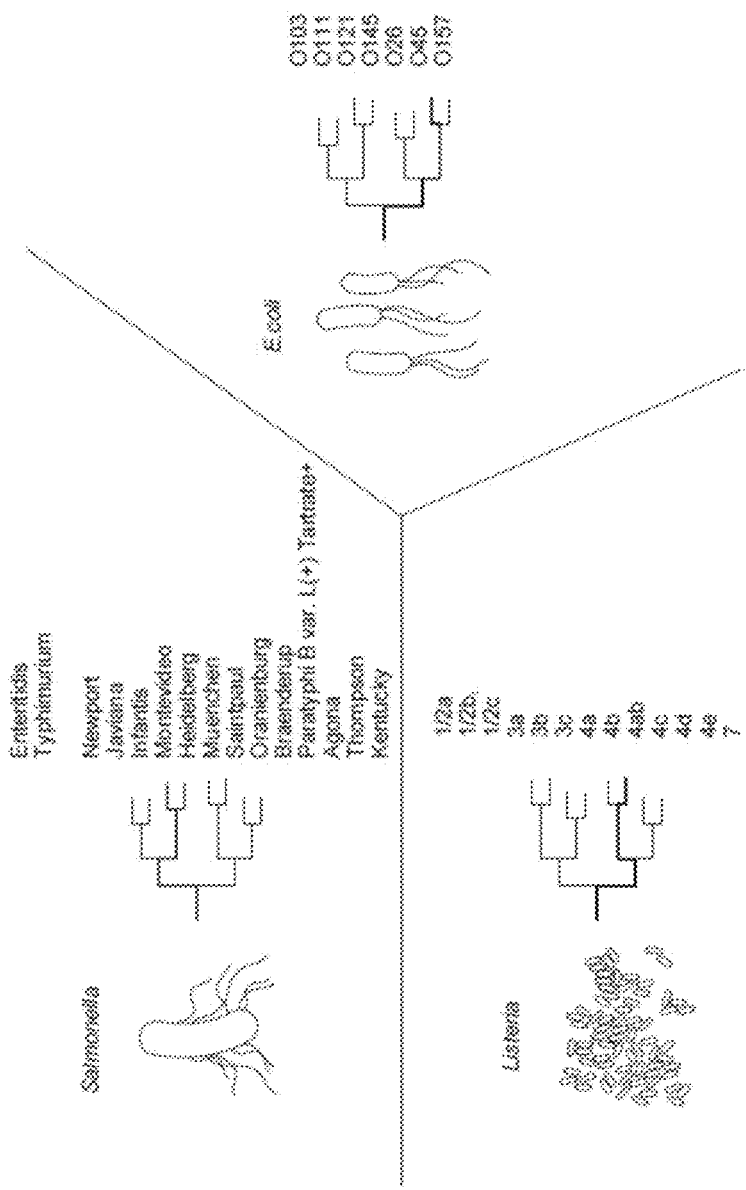
FIG. 8: is a schematic illustrating various serotypes of various microorganisms that can be detected by an analysis of a plurality of nucleic acid sequences as described herein and further validated with a serotyping assay.

In some cases, the assay is a serotyping assay. A serotype or serovar is a distinct variation within a species of bacteria or virus. These microorganisms can be classified together based on their cell surface antigens, allowing the epidemiologic classification of microorganisms to the sub-species level. A group of serovars with common antigens is called a serogroup or sometimes serocomplex. In some aspects, the disclosure provides methods for performing a sequencing assay on a plurality of nucleic acids derived from a sample and a serotyping assay on a derivative of said sample. FIG. 8 is a schematic illustrating various serotypes of various microorganisms that can be detected by an analysis of a plurality of nucleic acid sequences as described herein and further validated with a serotyping assay.

Differentiating Live Versus Dead Microorganisms

Figure 9:
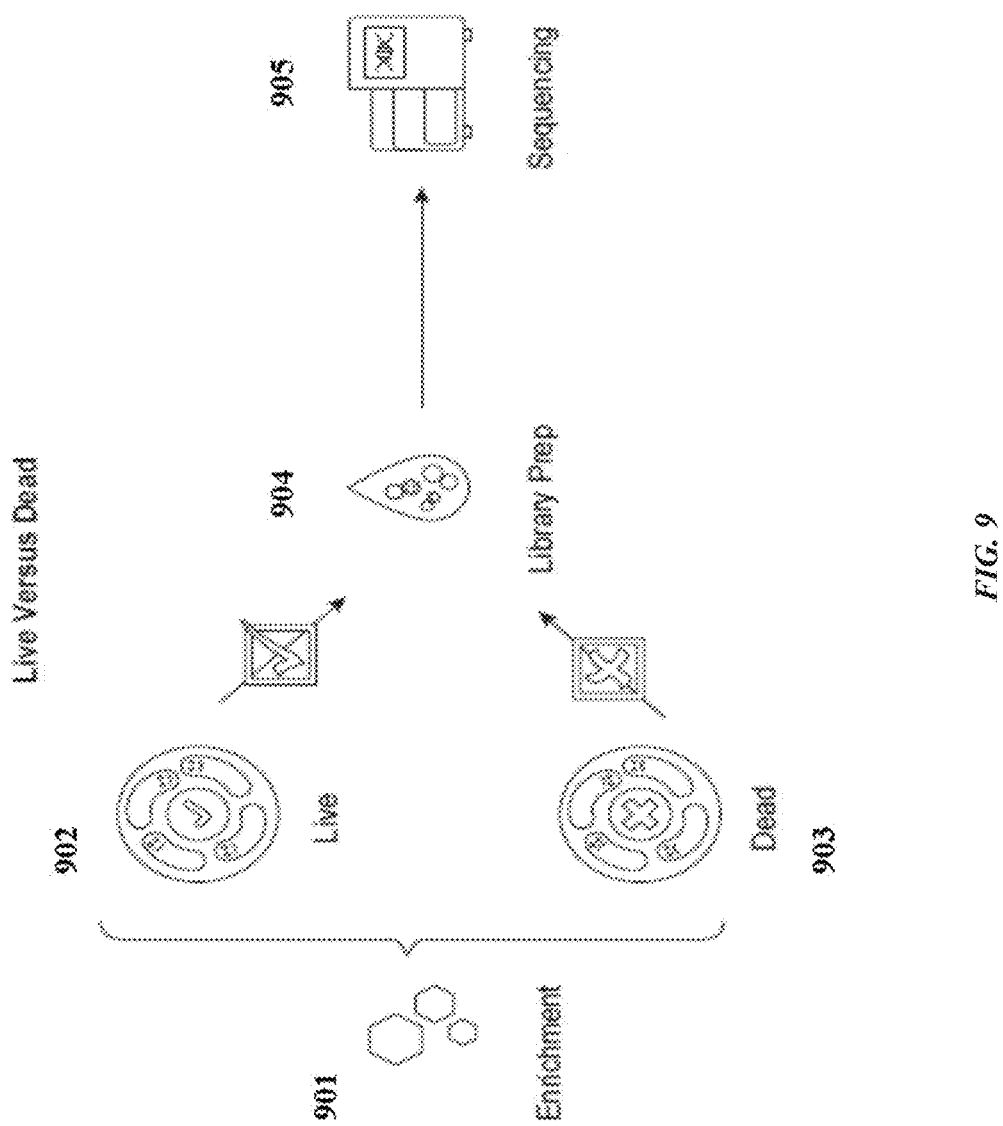
FIG. 9: is a schematic illustrating one process for distinguishing a live microorganism from a food or from an environmental sample.

Nucleic acid-based targeted analytical methods, such as PCR provide only limited information on the activities and physiological states of microorganisms in samples and cannot distinguish viable cells from dead cells. In some aspects, the disclosure provides methods for distinguishing a live microorganism in a food sample or in another sample, from a dead microorganism within the same sample. FIG. 9 is a schematic illustrating one process for distinguishing a live microorganism from a food or from an environmental sample. Briefly, FIG. 9 illustrates than an amount of a microorganism in a sample can be increased, i.e., enriched 901, by growing the microorganism in a rich medium for a period of time. A reagent, such as a photoreactive DNA-binding dye, a DNA intercalating reagent, or another suitable reagent may be added to enriched sample 901. Such reagents distinguish live 902 microorganisms from dead 903 microorganisms by interacting with the nucleic acid sequence of dead microorganisms only. In some cases, the disclosure contemplates using propidium monoazide or a derivative thereof as a dye. The modified sample can be prepared for a subsequent reaction 904, such as a sequencing reaction 905.

In some instances the disclosure provides a method comprising adding a reagent to a plurality of nucleic acid molecules from a food sample, or food related sample or another sample described herein thereby forming a modified plurality of nucleic acid molecules, whereby said reagent (i) interacts with and modifies a structure of a plurality of nucleic acid molecules derived from one or more dead microorganisms; and (ii) does not interact with or modify a structure of a nucleic acid molecule derived from one or more live microorganisms; thereby providing a modified plurality of nucleic acid molecules; and sequencing said modified plurality of nucleic acid molecules, thereby distinguishing one or more live organisms from said food sample or from another sample.

In other aspects the disclosure provides a method comprising performing a pore sequencing or other DNA sequencing or hybridization assay on a plurality of nucleic acid molecules from a food sample or from another sample whereby said pore sequencing reaction distinguishes one or more nucleic acid molecules derived from a dead microorganism from one or more nucleic acid molecules derived from a live microorganism based on a methylation or other epigenetic pattern of said one or more nucleic acid molecules derived from said dead microorganism.

In some embodiments, epigenetic patterns, such as methylation, can be detected in DNA derived from food or environmental samples by chemical or enzymatic selection methods prior to sequencing. Such methods include, but are not limited to, bisulfite sequencing (including targeted bisulfite sequencing, see e.g. Ziller et al. Epigenetics Chromatin. 2016 Dec. 3; 9:55 and Masser et al. J Vis Exp. 2015; (96): 52488) and methylation-sensitive restriction digestion (see e.g. Bitinaite et al. U.S. Pat. No. 9,034,597).

Barcodes

Unique identifiers, such as barcodes, can be added to one or more nucleic acids isolated from a sample from a food processing facility, from a hospital or clinic, or from another sources. Barcodes can be used to associate a sample with a source; e.g., to associate an environmental sample with a specific food processing facility or with a particular location within said food processing facility. Barcodes can also be used to identify a processing of a sample, as described in U.S. Patent Pub. No. 2016/0239732, which is entirely incorporated herein by reference.

Figure 10:
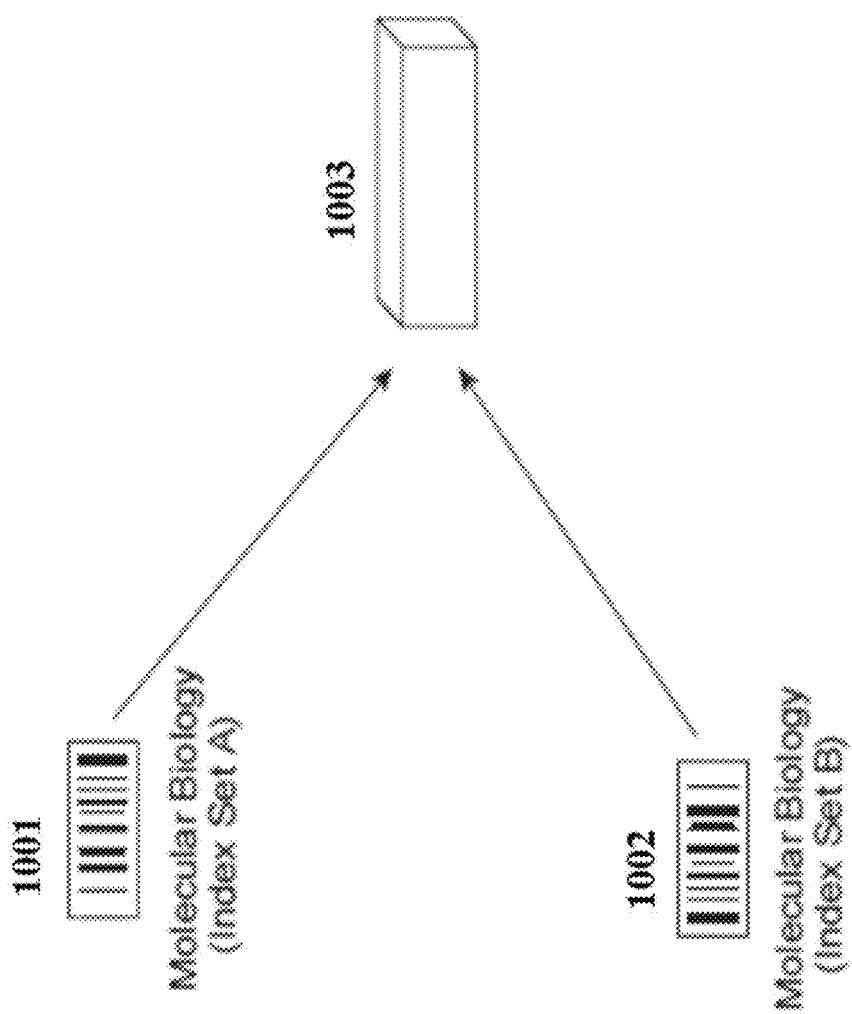
FIG. 10: illustrates a process for re-using flow cells with distinct indexes.
Figure 18:
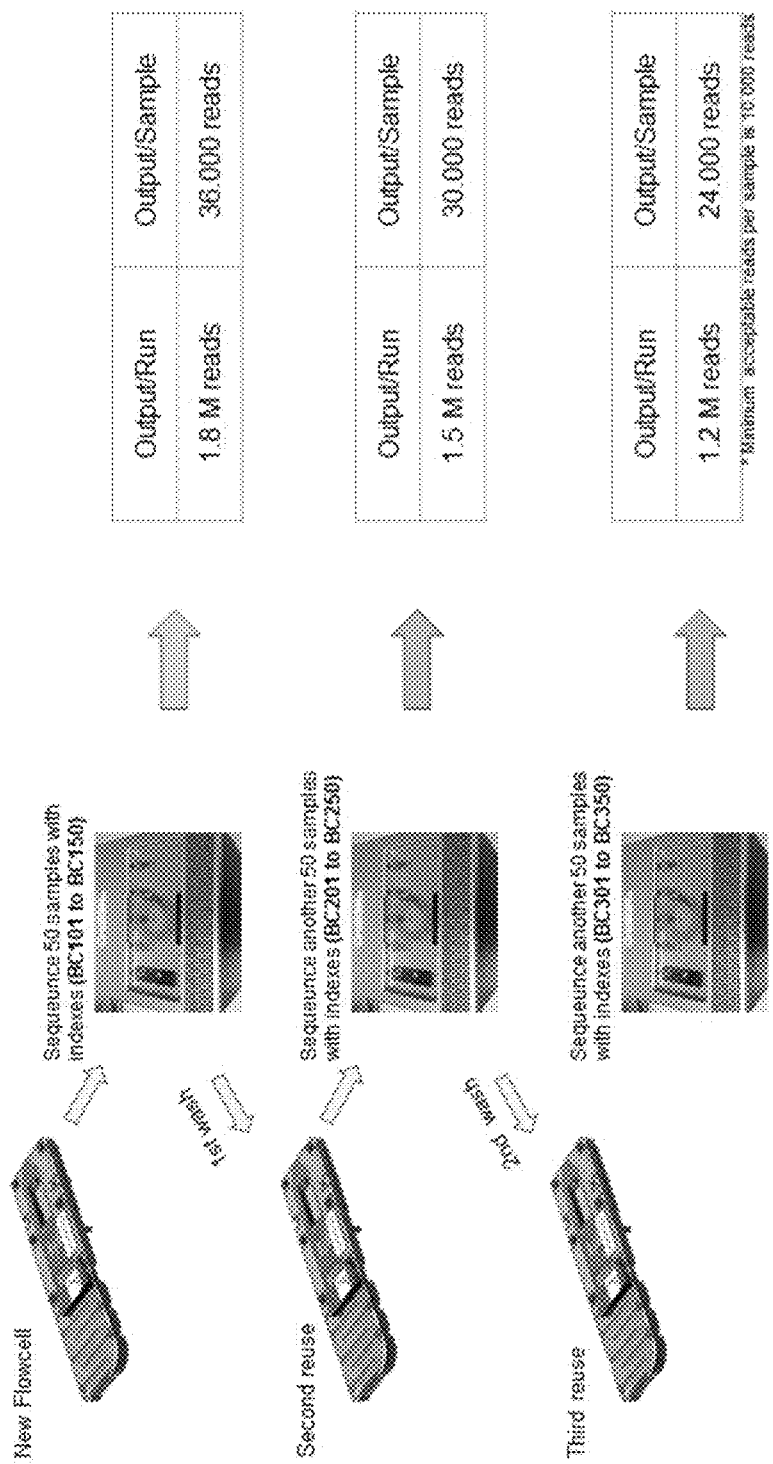
FIG. 18: illustrates the reuse of MinION/GridION flow cells.
Figure 19:
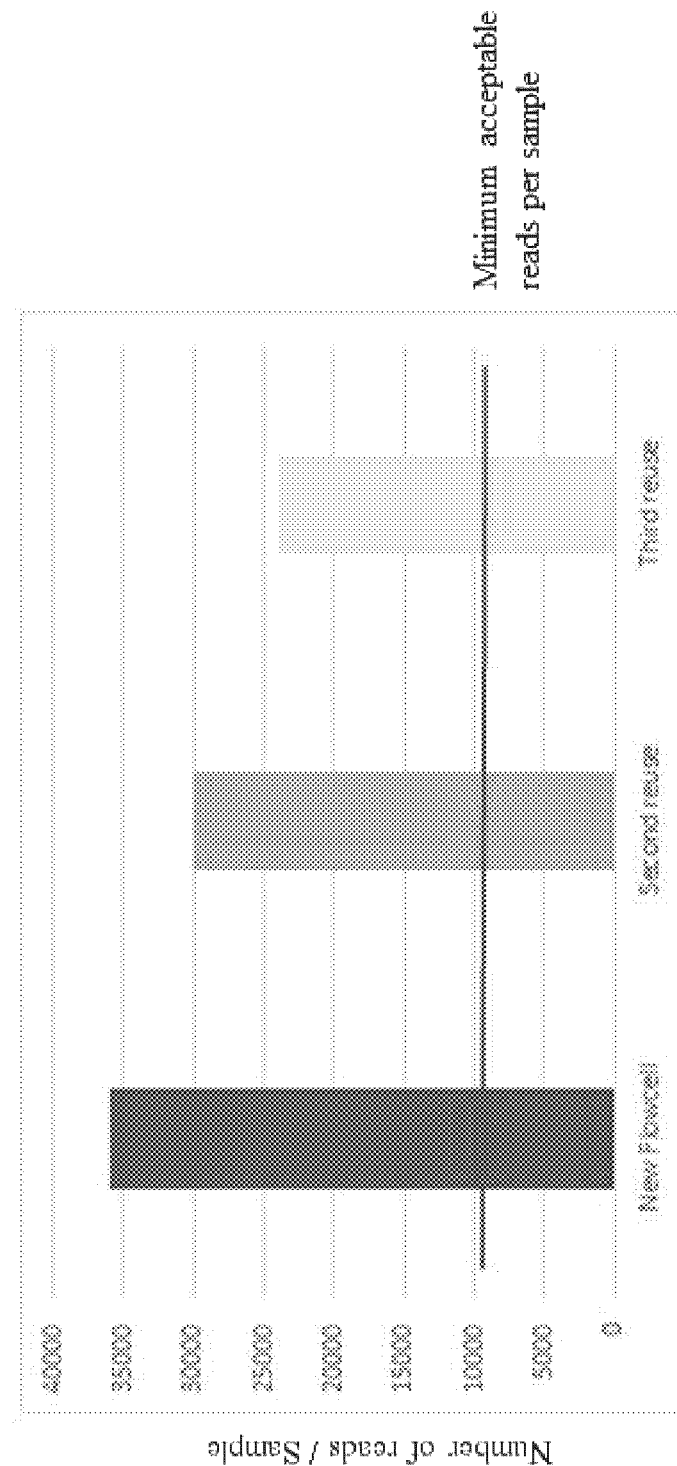
FIG. 19: illustrates the number of reads per sample during reuse of MinION/GridION flow cells.

In some aspects, the disclosure provides a method comprising adding a first barcode to a first plurality of nucleic acid sequences from a sample, thereby providing a first plurality of barcoded nucleic acid sequences; performing a first sequencing reaction on said first plurality of barcoded nucleic acid sequences, wherein said sequencing reaction is performed on a sequencing apparatus comprising a flow cell; adding a second barcode to a second plurality of nucleic acid sequences from a second sample, thereby providing a second plurality of barcoded nucleic acid sequences; and performing a second sequencing reaction on said second plurality of barcoded nucleic acid sequences, wherein said second sequencing reaction is performed on said sequencing apparatus comprising said flow cell, thereby reusing said flow cell. FIG. 10 illustrates a process for re-using flow cells with distinct indexes as described herein. As illustrated by FIG. 10 two distinct indexes, 1001 and 1002, such as two different barcodes, can be added to different samples prior to sequencing 1003. Since a first sample can be associated with a first index 1001 and a second sample can be associated with a second index 1002 this process effectively allows for the re-using of a flow cell. FIG. 18 and FIG. 19 demonstrate the re-use of MinION/GridION flow cells. Example 21 demonstrates how certain primer design schemes, such as a nonperiodic design, can reduce crosstalk in situations with high multiplexing or closely related sequences, as may happen with reuse of flow cells.

One or more barcodes or block of barcodes may be added to a nucleic acid sequence from a food sample or another sample from a food processing facility, such as a first, a second, a third, or any subsequent sample. In some cases, 1, 2, 3, 4, 5, 6, 7, 8, 9, 10, 11, 12, 13, 14, 15, 16, 17, 18, 19, or 20 identical barcodes are added to such samples. In other cases, distinct barcodes are added to such samples. In some cases, 1, 2, 3, 4, 5, 6, 7, 8, 9, 10, 11, 12, 13, 14, 15, 16, 17, 18, 19, or 20 distinct barcodes are added to such samples. The serial addition of two or more barcodes, either identical in sequence or distinct in sequence, can provide an indexing of a sample that is used in its analyses. The presence of additional barcode or barcode blocks make the system more robust against any barcode manufacturing error and can also significantly reduce the chance of cross contamination between barcodes. In some cases, a barcode is added to a nucleic acid sequence comprising complementary DNA (cDNA) sequences, ribonucleic acid (RNA) sequences, genomic deoxyribonucleic acid (gDNA) sequences, or a mixture of cDNA, RNA, and gDNA sequences.

Apparatus

Figure 11:
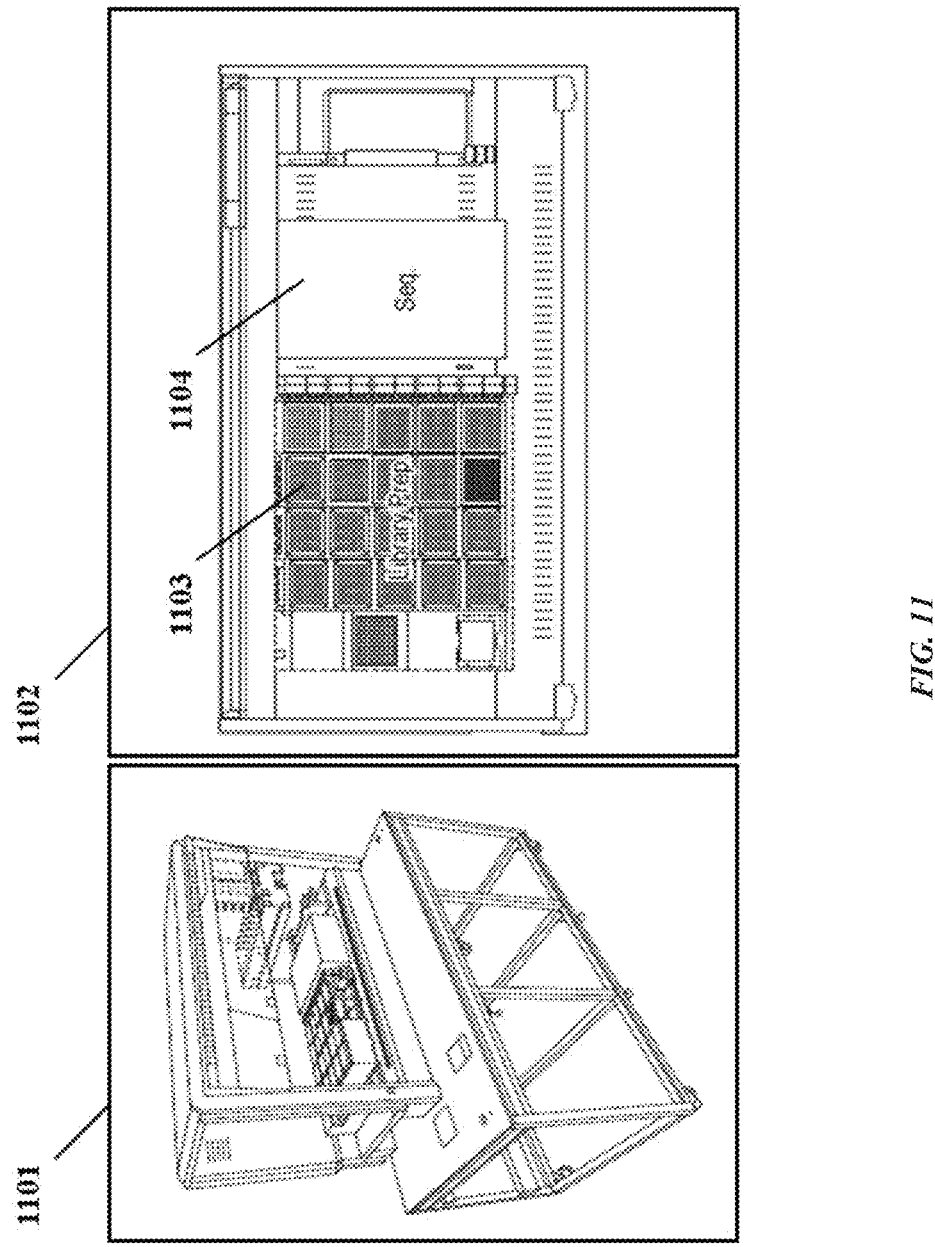
FIG. 11: illustrates an automated sequencing apparatus of the disclosure.
Figure 12:
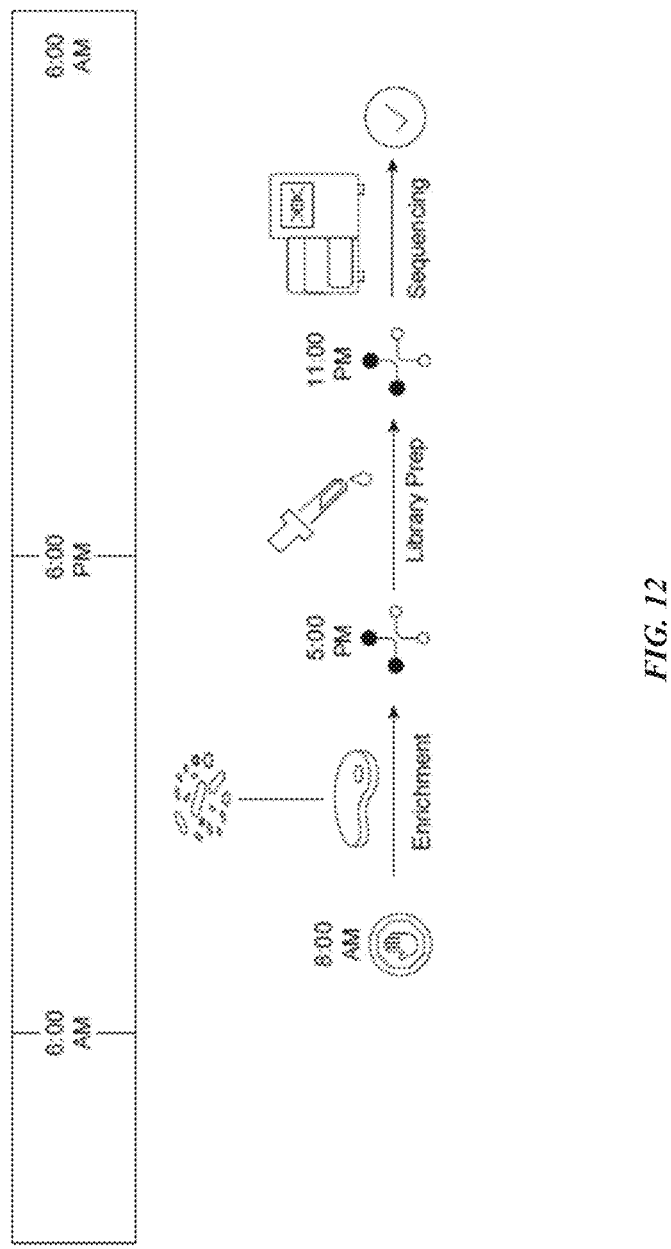
FIG. 12: illustrates a sequencing process with no human touch points after enrichment.

Automated nucleic acid sequencing apparatuses can provide a robust platform for the generation of nucleic acid sequencing reads. Unfortunately, many apparatuses have a high rate of failure, i.e., high rate of error of the sequencing reaction itself, which require manual intervention in such instances, such as re-loading of samples into flow cells. In some aspects, the disclosure provides an automated nucleic acid sequencing apparatus that requires no manual intervention in the event of a failure of a sequencing reaction. In some aspects, the disclosure provides a nucleic acid sequencing apparatus comprising: a nucleic acid library preparation compartment comprising two or more chambers configured to prepare a plurality of nucleic acids for a sequencing reaction, wherein said compartment is operatively connected to a nucleic acid sequencing chamber; a nucleic acid sequencing chamber, wherein said nucleic acid sequencing chamber comprises: (i) one or more flow cells comprising a plurality of pores configured for the passage of a nucleic acid strand, wherein said two or more flow cells are juxtaposed to one another; and an automated platform, wherein said automated platform is programmed to robotically move a sample from said nucleic acid library preparation compartment into said nucleic acid sequencing chamber. FIG. 11 illustrates an automated sequencing apparatus of the disclosure. 1101 is a diagram of the apparatus comprising the nucleic acid sequencing compartment 1102. Nucleic acid library preparation compartment 1103 shows a variety of chambers configured to prepare a plurality of nucleic acids for a sequencing reaction in close proximity to a sequencing chamber 1104, which comprises one or more flow cells. Briefly, an automated apparatus of the disclosure is programmed to move one or more samples from the library preparation chambers 1103 into a sequencing chamber 1104 upon detecting a failure in a sequencing reaction. This provides a sequencing process with no human touch points after a sample is added to the library preparation chamber, as illustrated in FIG. 12. FIG. 12 illustrates an embodiment where a sample from a food processing facility, from a hospital or clinical setting, or from another source can be manually processed between 6 am to 6 pm or any shorter or longer incubation window by incubating the sample in a presence of a growth medium (e.g., enrichment) and automatically processed after the sample is added to a nucleic acid preparation chamber 1103.

The disclosed apparatus is programmed in such a manner that said automated platform moves one or more samples from said nucleic acid library preparation compartment into said nucleic acid sequencing chamber. Upon detecting a failure of a sequencing reaction, the automated platform moves one or more samples from the failed sequencing flow cell or apparatus to the next sequencing flow cell or apparatus. In many cases, such samples comprise nucleic acid sequences that include one or more barcodes. In some cases, a plurality of mutually exclusive barcodes are added to a plurality of nucleic acids in said two or more chambers of the nucleic acid library preparation compartment 1103, thereby providing a plurality of mutually exclusive barcoded nucleic acids within the apparatus. In some instances, the automated platform robotically moves two or more of said mutually exclusive barcoded nucleic acids into said nucleic acid sequencing chamber, in some instances by moving said mutually exclusive barcoded nucleic acids into a same flow cell of said one or more flow cells.

Classification

Microbiome data (data representing the presence or absence of particular species or serotypes of microbes as determined by sequencing) of the invention can be used to classify a sample. For example, a sample can be classified as, or predicted to be: a) containing a particular pathogenic microbe, b) containing a particular serotype of a pathogenic microbe, and/or c) contaminated with at least one species/serotype of pathogenic microbe. Many statistical classification techniques are known to those of skill in the art. In supervised learning approaches, a group of samples from two or more groups (e.g. contaminated with a pathogen and not) are analyzed with a statistical classification method. Microbe presence/absence data can be used as a classifier that differentiates between the two or more groups. A new sample can then be analyzed so that the classifier can associate the new sample with one of the two or more groups. Commonly used supervised classifiers include without limitation the neural network (multi-layer perceptron), support vector machines, k-nearest neighbours, Gaussian mixture model, Gaussian, naive Bayes, decision tree and radial basis function (RBF) classifiers. Linear classification methods include Fisher's linear discriminant, logistic regression, naive Bayes classifier, perceptron, and support vector machines (SVMs). Other classifiers for use with the invention include quadratic classifiers, k-nearest neighbor, boosting, decision trees, random forests, neural networks, pattern recognition, Bayesian networks and Hidden Markov models. One of skill will appreciate that these or other classifiers, including improvements of any of these, are contemplated within the scope of the invention.

Classification using supervised methods is generally performed by the following methodology:

In order to solve a given problem of supervised learning (e.g. learning to recognize handwriting) one has to consider various steps:

1. Gather a training set. These can include, for example, samples that are from a food or environment contaminated or not contaminated with a particular microbe, samples that are contaminated with different serotypes of the same microbe, samples that are or are not contaminated with a combination of different species and serotypes of microbes, etc. The training samples are used to "train" the classifier.

2. Determine the input "feature" representation of the learned function. The accuracy of the learned function depends on how the input object is represented. Typically, the input object is transformed into a feature vector, which contains a number of features that are descriptive of the object. The number of features should not be too large, because of the curse of dimensionality; but should be large enough to accurately predict the output. The features might include a set of bacterial species or serotypes present in a food or environmental sample derived as described herein.

3. Determine the structure of the learned function and corresponding learning algorithm. A learning algorithm is chosen, e.g., artificial neural networks, decision trees, Bayes classifiers or support vector machines. The learning algorithm is used to build the classifier.

4. Build the classifier (e.g. classification model). The learning algorithm is run on the gathered training set. Parameters of the learning algorithm may be adjusted by optimizing performance on a subset (called a validation set) of the training set, or via cross-validation. After parameter adjustment and learning, the performance of the algorithm may be measured on a test set of naive samples that is separate from the training set.

Once the classifier (e.g. classification model) is determined as described above, it can be used to classify a sample, e.g., that of food sample or environment that is being analyzed by the methods of the invention.

Unsupervised learning approaches can also be used with the invention. Clustering is an unsupervised learning approach wherein a clustering algorithm correlates a series of samples without the use the labels. The most similar samples are sorted into "clusters." A new sample could be sorted into a cluster and thereby classified with other members that it most closely associates.

Digital Processing Device

In some aspects, the disclosed provides quality control methods or methods to assess a risk associated with a food, with a hospital, with a clinic, or any other location where the presence of a bacterium poses a certain risk to one or more subjects. In many instances, systems, platforms, software, networks, and methods described herein include a digital processing device, or use of the same. In further embodiments, the digital processing device includes one or more hardware central processing units (CPUs), i.e., processors that carry out the device's functions, such as the automated sequencing apparatus disclosed herein or a computer system used in the analyses of a plurality of nucleic acid sequencing reads from samples derived from a food processing facility or from any other facility, such as a hospital a clinical or another. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device. In other embodiments, the digital processing device could be deployed on premise or remotely deployed in the cloud.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art. In many aspects, the disclosure contemplates any suitable digital processing device that can either be deployed to a food processing facility, or is used within said food processing facility to process and analyze a variety of nucleic acids from a variety of samples.

In some embodiments, a digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, a digital processing device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, a digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, a digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

In some embodiments, a digital processing device includes a digital camera. In some embodiments, a digital camera captures digital images. In some embodiments, the digital camera is an autofocus camera. In some embodiments, a digital camera is a charge-coupled device (CCD) camera. In further embodiments, a digital camera is a CCD video camera. In other embodiments, a digital camera is a complementary metal-oxide-semiconductor (CMOS) camera. In some embodiments, a digital camera captures still images. In other embodiments, a digital camera captures video images. In various embodiments, suitable digital cameras include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and higher megapixel cameras, including increments therein. In some embodiments, a digital camera is a standard definition camera. In other embodiments, a digital camera is an HD video camera. In further embodiments, an HD video camera captures images with at least about 1280×about 720 pixels or at least about 1920×about 1080 pixels. In some embodiments, a digital camera captures color digital images. In other embodiments, a digital camera captures grayscale digital images. In various embodiments, digital images are stored in any suitable digital image format. Suitable digital image formats include, by way of non-limiting examples, Joint Photographic Experts Group (JPEG), JPEG 2000, Exchangeable image file format (Exif), Tagged Image File Format (TIFF), RAW, Portable Network Graphics (PNG), Graphics Interchange Format (GIF), Windows® bitmap (BMP), portable pixmap (PPM), portable graymap (PGM), portable bitmap file format (PBM), and WebP. In various embodiments, digital images are stored in any suitable digital video format. Suitable digital video formats include, by way of non-limiting examples, AVI, MPEG, Apple® QuickTime®, MP4, AVCHD®, Windows Media®, DivX™, Flash Video, Ogg Theora, WebM, and RealMedia.

Non-Transitory Computer Readable Storage Medium

In many aspects, the systems, platforms, software, networks, and methods disclosed herein include one or more non-transitory computer readable storage media encoded with a program including instructions executable by the operating system of an optionally networked digital processing device. For instance, in some aspects, the methods comprise creating data files associated with a plurality of sequencing reads from a plurality of samples associated with a food processing facility. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the systems, platforms, software, networks, and methods disclosed herein include at least one computer program. A computer program includes a sequence of instructions, executable in the digital processing device's CPU, written to perform a specified task. In light of the disclosure provided herein, those of skill in the art will recognize that a computer program may be written in various versions of various languages. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. A web application for providing a career development network for artists that allows artists to upload information and media files, in some embodiments, includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C #, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB.NET, or combinations thereof. Compilation is often performed, at least in part, to create an executable program. In some embodiments, a computer program includes one or more executable complied applications.

Software Modules

The systems, platforms, software, networks, and methods disclosed herein include, in various embodiments, software, server, and database modules. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

EXAMPLES

Example 1

Preparation of Food and Environmental Samples

Food and environmental samples may be processed for various purposes, such as the enrichment of one or more microorganism from the sample, or the isolation of one or more microorganism from the sample. The following protocol was used in the preparation of various food and environmental samples including: carcass rinses, stainless steel, primary production boot covers, dry pet food and shell eggs.

Example 2

Obtaining a Carcass Food Sample

In this example, carcass food samples are generated by aseptically draining excess fluid from a carcass and transferring the carcass to a large sterile sampling bag. 100 mL of an enriched broth, in this case, Clear *Salmonella* media (CSM) was poured into the cavity of the carcass in the sampling bag. The carcass was rinsed inside and out with a rocking motion for about one minute, while assuring that all surfaces (interior and exterior of the carcass) were rinsed. About 20±0.5 mL of the CSM was added to the sample bag and homogenized by massaging sample bag for approximately 1.5-2 min. The sample was incubated at 42±1° C. for 9-24 h, providing an enriched sample.

Example 3

Obtaining an Environmental Sample from a Stainless Steel Surface

In this example, a stainless steel surface environmental sample was generated by moistening a sterile sampling sponge in 10 mL of Dey-Engley Broth prior to sampling, or using a sponge pre-moistened in the same. The sponge was used to touch, scrub, or otherwise contact the stainless steel surface and it was subsequently placed into a sampling bag. About 10±0.5 mL of CSM was added to the sampling sponge. Subsequently, the sponge was pressed to expel the collection broth into the CSM solution. The sample was incubated at 42±1° C. for 9-24 h, providing an enriched sample.

Example 4

Obtaining an Environmental Sample from a Boot Cover

In this example, an environmental sample from a boot cover was first pre-moistened in skim milk. About 50±1 mL of CSM was then added to the sampling bag containing boot cover environmental sample. The contents were mixed thoroughly for approximately 1.5-2 min, and incubated at 42±1° C. for 9-24 h, thereby providing an enriched sample. The enriched sample was removed from incubator and briefly mixed.

TABLE 1

Food and Environmental Sample Preparation
Table 1
Food and Environmental Sample Preparation

| Matrix | Sample Size | Enrichment Amount determined by volume or weight | Incubation |
| --- | --- | --- | --- |
| Carcass Rinse | 30 ± 0.6 mL sample rinse fluid | 20 ± 0.5 mL of Clear *Salmonella* media (CSM) | 42 ± 1° C. for 9-24 h |
| Stainless Steel | 1 sponge pre moistened with 10 mL tris-buffered saline | 10 ± 0.5 mL Clear *Salmonella* media (CSM) | 42 ± 1° C. for 9-24 h |
| Environmental Boot Cover | 1 environmental sampling bootie pre-moistened with 10 mL skim milk | 50 ± 1 mL Clear *Salmonella* media (CSM) | 42 ± 1° C. for 9-24 h |
| Pet Food | 25 ± 0.5 g | 100 ± 1 mL Clear *Salmonella* media (CSM) | 42 ± 1° C. for 9-24 h |
| Shell Eggs | 100 ± 2 g | 200 ± 2 mL Clear *Salmonella* media (CSM) | 42 ± 1° C. for 9-24 h |

Example 5

Obtaining a Pet Food Sample

In this example, about 25±0.5 g of a pet food sample were added into a filtered sampling bag. About 100±1 mL CSM was then added to the sampling bag containing said pet food. The contents were mixed thoroughly for approximately 1.5-2 min, and incubated at 42±1° C. for 9-24 h, thereby providing an enriched sample. The enriched sample was removed from incubator and briefly mixed.

Example 6

Obtaining a Shell Egg Food Sample

In this example, about 100±2 g of a homogenized egg sample was added to a filtered sampling bag. About 200±2 mL CSM was then added to the sampling bag containing said homogenized egg sample. The contents were mixed thoroughly for approximately 1.5-2 min, and incubated at 42±1° C. for 9-24 h, thereby providing an enriched sample. The enriched sample was removed from incubator and briefly mixed.

Example 7

Photoreactive DNA-Binding Dye Treatment

In this example, a photoreactive DNA-binding dye, namely propidium monoazide (PMA) was added to various food and environmental samples, including the samples described in Examples 1-6. In general, 5 µL of a PMAxx solution was added to a well in a 200 µL 96-well PCR plate. Approximately 45 µL of each enriched sample from the sampling bags described in Examples 1-6 was added to individual wells in PCR plate containing PMAxx. The samples were mixed thoroughly by gentle pipetting and placed in the dark for 10 min at room temperature. Subsequently, the plates were incubated under a blue LED light for 20 min. 10 µL of each sample were then diluted with 90 µL of Lysis Buffer in a new 200 µL 96-well PCR plate. The plate was then incubated in a thermocycler as shown below. Alternatively the sample could have been incubated in a water bath.

| Step | Temperature | Time |
|---|---|---|
| 1 | 37° C. | 20 min |
| 2 | 95° C. | 10 min |

Example 8

PMAxx-Induced Removal of Free-Floating DNA

Figure 13:
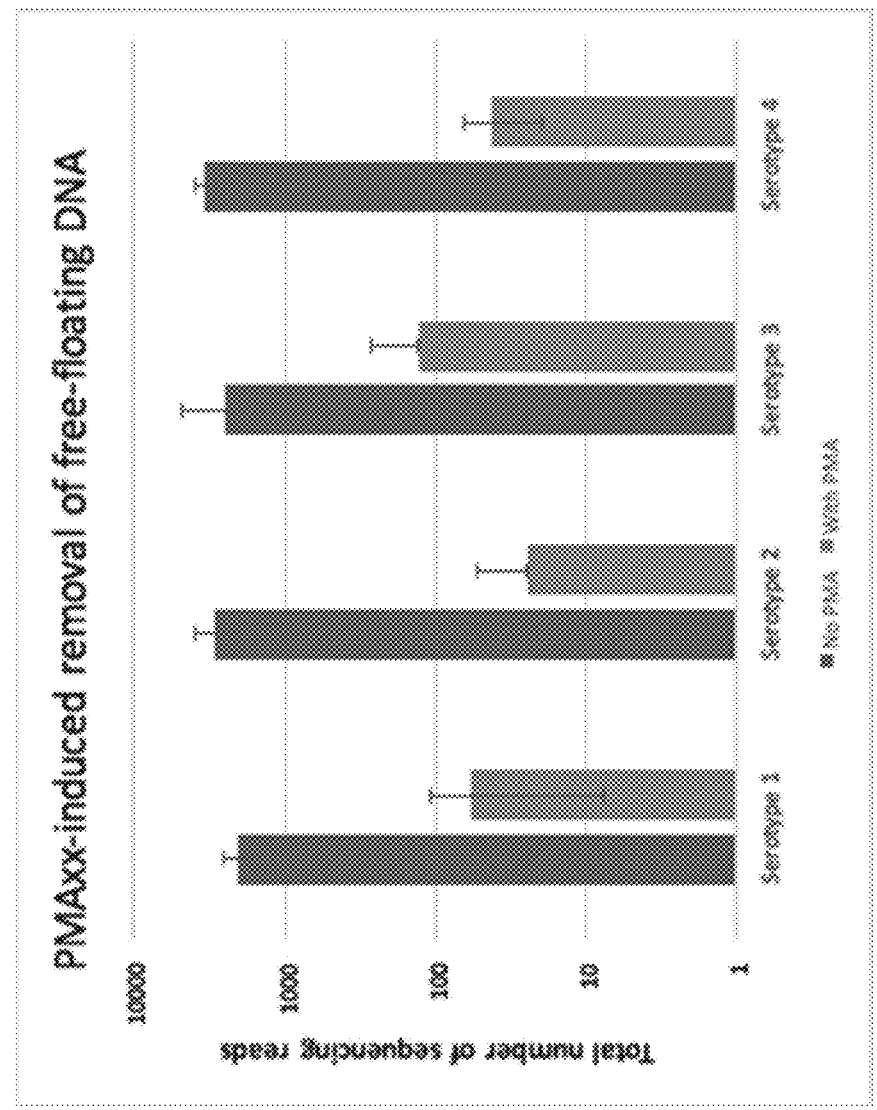
FIG. 13: illustrates the PMAxx-induced removal of free-floating DNA.

This example demonstrates that addition of a solution of the photoreactive DNA-binding dye PMAxx to a sample solution reduced the number of free-floating and contaminating DNA in said sample. Specifically, 45 µL of each enriched sample from the sampling bags as described in Examples 1-7 was added to individual wells of the 96-well PCR plate containing 25 µL of PMAxx solution. The sample solutions were mixed thoroughly by gentle pipetting and placed in the dark for 10 min at room temperature. Subsequently, the plates were incubated under a blue LED light for 20 min. 10 µL of each sample were then diluted with 90 µL of Lysis Buffer in a new 200 µL 96-well PCR plate. The plate was then incubated in a thermocycler as shown below. Analysis of the sample readouts showed that the addition of PMAxx solution (25 µL) to the sample solution was sufficient to reduce the number of free-floating DNA by at least 2 orders of magnitude, as shown in FIG. 13.

Example 9

Amplification Reaction

In this example, the samples described in Examples 1-8 were subjected to an amplification reaction. Briefly 15 µL of primer cocktail and polymerase master mix was added to individual wells of an empty 200 µL 96-well PCR plate. About 5 µl of each sample treated with a photoreactive DNA-binding dye treatment was added to the respective wells containing the polymerase master mix. The solution was mixed gently by pipetting up and down and placed in a thermocycler with the conditions described below.

| Step | Temperature | Time |
|---|---|---|
| 1 | 95° C. | 3 min |
| 2 | 95° C. | 30 sec |
| 3 | 57° C. | 1 min |
| 4 | 72° C. | 1 min |
| 5 | Go to step 2, 37 times | |
| 6 | 72° C. | 10 min |
| 7 | 10° C. | Hold |

Example 10

Library Preparation

In this example, Solid Phase Reversible Immobilization (SPRI) Magnetic Beads were used to purify and quantify one or more of the samples described in Examples 1-9. Briefly, the SPRI beads were removed from 4° C. storage and allowed to reach room temperature for approximately 15 min. About 1 mL of 80% ethanol was prepared by combining 800 µL of ethanol and 200 µL of molecular biology grade water. Equal volumes of each samples amplification product (described in Example 9) was used to obtain at least 100 µL of pooled products, which was purified using the SPRI beads along with standard manufacturing protocols. Briefly, 100 µL of vortexed, pooled PCR product was pipetted into a 0.2 mL PCR tube and add 60 µL of SPRI beads. The tube was mixed thoroughly by pipetting up and down approximately 10 times and incubated at room temperature for 5 min. The sample/bead mixture was placed in a magnetic stand and the beads were allowed to pellet in a ring for approximately 30-60 s, leaving a clear supernatant. The supernatant was discarded by leaving the tube in the magnetic stand while placing the pipette tip to the bottom center of the tube when aspirating to avoid disturbing the beads. 190 µL of 80% ethanol was then added to the tube, and incubated for 5-10 s. The tube was aspirated fully and the ethanol solution discarded. The process was repeated twice. The sample was allowed to dry for 3-5 min at room temperature, or until no visible ethanol remained. Once thoroughly dry, the tube was removed from the magnetic stand and re-suspended in 50 µL of 10 mM RSB into the tube. The tube was mixed thoroughly by gently pipetting up and down approximately 10 times and incubate at room temperature for 2 min. The tube was moved to a magnetic stand and incubated at room temperature for 2 min to allow the beads to pellet. Remove and retain 50 µL of the eluate.

Example 11

End Repair

In this example, the terminal ends of fragment nucleic acids described in Example 10 were repaired as described below. First, the following reagents were combined and mixed well by pipetting up and down approximately 10 times.

| Reagent | Volume |
| --- | --- |
| Purified Pooled Libraries | 45 µL |
| NEB Ultra II end-prep reaction buffer | 7 µL |
| NEB Ultra II End-prep enzyme mix | 3 µL |
| ONT DNA CS (DCS) | 5 µL |
| Total | 60 µL |

The samples were then spun for approximately 5 s using a benchtop minifuge. End-repair was performed in a thermal cycler with the following conditions:

| Step | Temperature | Time |
| --- | --- | --- |
| 1 | 20° C. | 5 min |
| 2 | 65° C. | 5 min |
| 3 | 25° C. | 5 min |

Subsequently, the samples were spun for approximately 5 s using a benchtop minifuge. 60 µL of SPRI beads were added to the end-repaired product and mixed by pipetting up and down approximately 10 times. The samples were incubated for 5 min at room temperature. The sample/bead mixture was placed in a magnetic stand and the beads were allowed to pellet in a ring around the middle portion of the tube for approximately 30-60 s, leaving a clear supernatant. The supernatant was discarded by leaving the tube in the magnetic stand while placing the pipette tip to the bottom center of the tube when aspirating to avoid disturbing the beads. 190 µL of 80% ethanol was added to the samples. The 80% ethanol solution was incubated in the tube for 5-10 s, and the ethanol was aspirated and discarded. This process was repeated twice. The sample was allowed to dry for 5 min at room temperature, or until no visible ethanol remained. The beads were resuspended with 31 µL molecular biology grade water and mixed by gently pipetting up and down approximately 10 times and incubate for 2 min at room temperature. The tube was moved to a magnetic stand and the beads were allowed to pellet for approximately 30-60 s. The eluate was retained as the "end-repaired product".

Example 12

Ligation

In this example, using the end-repaired product of Example 11, the following reagents were combined:

| Reagent | Volume |
| --- | --- |
| End-repaired product | 30 µL |
| ONT Adapter Mix (AMX 1D) | 20 µL |
| NEB Blunt/TA Ligase Master Mix | 50 µL |
| Total | 100 µL |

The reagents were gently mixed by pipetting up and down approximately 10 times and were incubated at room temperature for 10 min. About 40 µL of SPRI beads were added to the mixture, gently mixed, and incubated at room temperature for 5 min. The sample/bead mixture was placed in a magnetic stand and the beads were allowed to pellet in a ring around the middle portion of the tube for approximately 30-60 s, leaving a clear supernatant. The supernatant was discarded by leaving the tube in the magnetic stand while placing the pipette tip to the bottom center of the tube when aspirating to avoid disturbing the beads. The tube was removed from the magnetic rack and 140 µL of ONT-Adapter Bead Binding buffer was pipetted onto the beads. The sample was mixed by gently pipetting up and down approximately 10 times to resuspend the pellet. The tube was returned to the magnetic stand and the beads were allowed to pellet in a ring around the middle portion of the tube for approximately 30-60 s, leaving a clear supernatant. The supernatant was discarded by leaving the tube in the magnetic stand while placing the pipette tip to the bottom center of the tube when aspirating to avoid disturbing the beads. The tube was removed from the magnetic rack and an additional 140 µL of Adapter Bead Binding buffer was added and pipetted up and down to resuspend the pellet. The sample/bead mixture was placed in a magnetic stand and the beads were allowed to pellet into a ring around the middle portion of the tube for approximately 30-60 s, leaving a clear supernatant. The supernatant was discarded by leaving the tube in the magnetic stand while placing the pipette tip to the bottom center of the tube when aspirating to avoid disturbing the beads. The tube was then removed from the magnetic stand. About 15 µL of Elution Buffer (ELB) was added to the beads, and the beads were mixed thoroughly by pipetting up and down approximately 10 times and incubate for 10 minutes at room temperature for 5 min. The tubes were moved to a magnetic stand and the beads allowed to pellet for approximately 30-60 s. About 15 µL of eluate was remove and retained as the "final ligated product" for sequencing.

Example 13

Pore Sequencing

In this example, a food or an environmental sample was processed by pore sequencing using standard manufacturer protocols. Briefly, one or more flow cells were primed by combining the following reagents per flow cell:

| Reagent | Volume |
| --- | --- |
| ONT-Running Buffer with Fuel Mix (RBF) | 480 µL |
| Molecular grade H$_2$O | 520 µL |
| Total | 1,000 µL |

A loading library was prepared by combining the following reagents:

| Reagent | Volume |
| --- | --- |
| ONT-Running Buffer with Fuel Mix (RBF) | 35 µL |
| ONT-Library Loading Beads (LLB) | 25.5 µL |
| Final ligated product | 12 µL |
| Molecular grade H$_2$O | 2.5 µL |
| Total | 75 µL |

Figure 14:
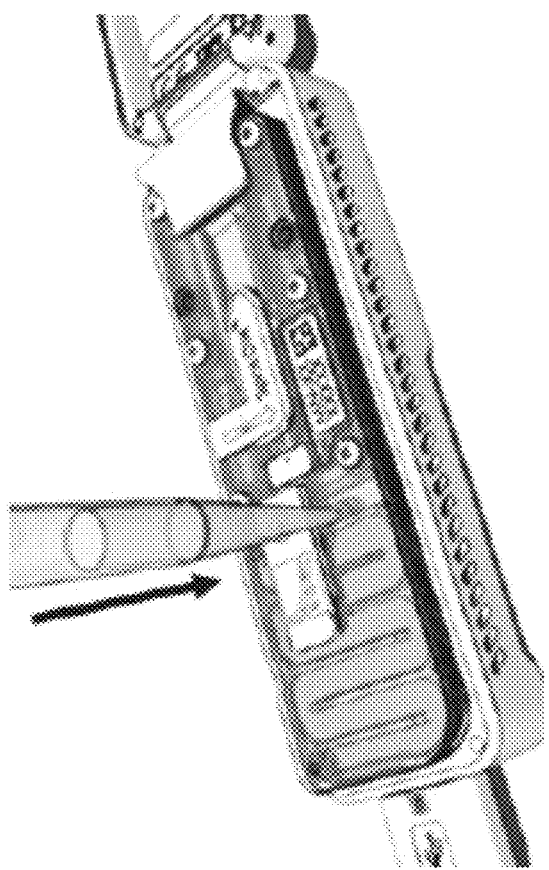
FIG. 14: illustrates a priming port in a flow cell.
Figure 15:
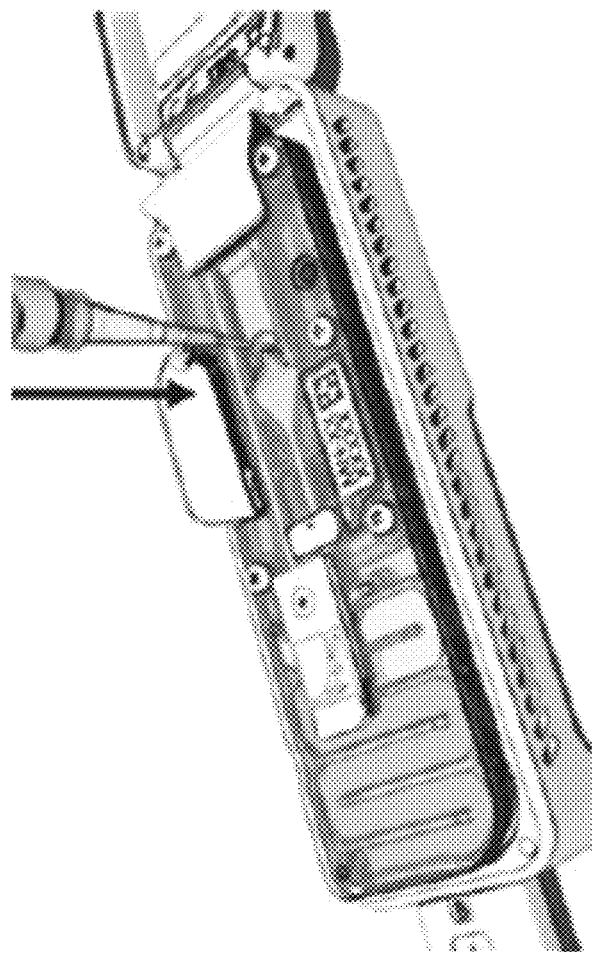
FIG. 15: illustrates a dispensing of a loading library on a flow cell.

The priming port on the Flow Cell was gently opened and approximately 50 µL of the preservative buffer and any small bubbles were removed, as illustrated by FIG. 14. About 800 µL of the priming mix was added into the priming port of the Flow Cell. Subsequently, 200 µL of the priming mix was dispensed into the Priming port. The final loading library was mixed thoroughly and 75 µL were added into the SpotON port, as illustrated by FIG. 15. The lid of the pore sequencing device was closed and the sequencing was executed.

Example 14

Data Analysis and Interpretation

Figure 16:
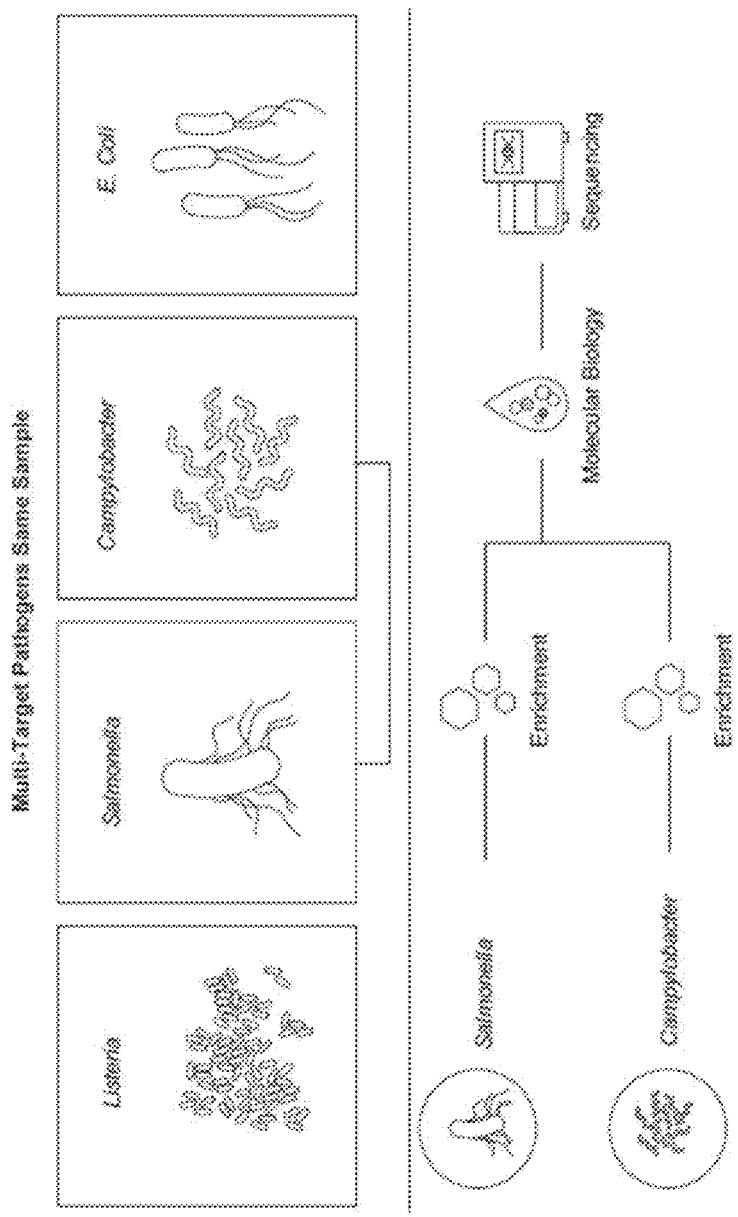
FIG. 16: illustrates the simultaneous targeting of multiple pathogens.

In this example, an electronic communication comprising a data set associated with the sequencing reaction described in Example 13 was transmitted over the cloud for analysis. The results of the analysis were reported back to customer. FIG. 16 in this particular example, the customer requested an analysis of the sample for the presence or absence of *Listeria, Salmonella, Campylobacter*, and *E. coli*, which required the simultaneous targeting of multiple pathogens.

Example 15

Identification of a Microorganism in a Food, Environmental Sample, or in a Non-Food Associated Sample by Microbiome Metagenomics and Supervised Learning In this example, data from pore sequencing was used to identify foodborne disease-causing microorganisms. Briefly, the methods and processes described in Examples 1-13 were used to identify food or environmental samples comprising one or more of the organism shown below.

TABLE 2

Exemplary Pathogenic Microorganisms Identified by Methods According to This Disclosure
Table 2

| Organism | Common Name of Illness | Onset Time After Ingesting | Signs & Symptoms | Duration of Illness | Food Sources |
| --- | --- | --- | --- | --- | --- |
| *Bacillus cereus* | *B. cereus* food poisoning | 10-16 hrs | Abdominal cramps, watery diarrhea, nausea | 24-48 hours | Meats, stews, gravies, vanilla sauce |
| *Campylobacter jejuni* | Campylobacteriosis | 2-5 days | Diarrhea; cramps, fever, and vomiting; diarrhea may be bloody | 2-10 days | Raw and undercooked poultry, unpasteurized milk, contaminated water |
| *Clostridium botulinum* | Botulism | 12-72 hours | Vomiting, diarrhea, blurred vision, double vision, difficulty in swallowing, muscle weakness. Can result in respiratory failure and death | Variable | Improperly canned foods, especially home-canned vegetables, fermented fish, baked potatoes in aluminum foil |
| *Perfringens* | *Perfringens* food poisoning | 8-16 hours | Intense abdominal cramps, watery diarrhea | Usually 24 hours | Meats, poultry, gravy, dried or precooked foods, time and/or temperature-abused foods |
| *Cryptosporidium* | Intestinal cryptosporidiosis | 2-10 days | Diarrhea (usually watery), stomach cramps, upset stomach, slight fever | May be remitting and relapsing over weeks to months | Uncooked food or food contaminated by an ill food handler after cooking, contaminated drinking water |

TABLE 2-continued

Exemplary Pathogenic Microorganisms Identified by Methods According to This Disclosure
Table 2

| Organism | Common Name of Illness | Onset Time After Ingesting | Signs & Symptoms | Duration of Illness | Food Sources |
|---|---|---|---|---|---|
| *Cyclospora cayetanensis* | Cyclosporiasis | 1-14 days, usually at least 1 week | Diarrhea (usually watery), loss of appetite, substantial loss of weight, stomach cramps, nausea, vomiting, fatigue | May be remitting and relapsing over weeks to months | Various types of fresh produce (imported berries, lettuce, basil) |
| *E. coli* (*Escherichia coli*) producing toxin | *E. coli* infection (common cause of "travelers' diarrhea") | 1-3 days | Watery diarrhea, abdominal cramps, some vomiting | 3-7 or more days | Water or food contaminated with human feces |
| *E. coli* O157:H7 | Hemorrhagic colitis or *E. coli* O157:H7 infection | 1-8 days | Severe (often bloody) diarrhea, abdominal pain and vomiting. Usually, little or no fever is present More common in children 4 years or younger. Can lead to kidney failure. | 5-10 days | Undercooked beef (especially hamburger), unpasteurized milk and juice, raw fruits and vegetables (e.g. sprouts), and contaminated water |
| Hepatitis A | Hepatitis | 28 days average (15-50 days) | Diarrhea, dark urine, jaundice, and flu-like symptoms, i.e., fever, headache, nausea, and abdominal pain | Variable, 2 weeks-3 months | Raw produce, contaminated drinking water, uncooked foods and cooked foods that are not reheated after contact with an infected food handler; shellfish from contaminated waters |
| *Listeria monocytogenes* | Listeriosis | 9-48 hrs for gastro-intestinal symptoms, 2-6 weeks for invasive disease | Fever, muscle aches, and nausea or diarrhea. Pregnant women may have mild flu-like illness, and infection can lead to premature delivery or stillbirth. The elderly or immunocompromised patients may develop bacteremia or meningitis. | Variable | Unpasteurized milk, soft cheeses made with unpasteurized milk, ready-to-eat deli meats |
| Noroviruses | Variously called viral gastroenteritis, winter diarrhea, acute non-bacterial gastroenteritis, food poisoning, and food infection | 12-48 hrs | Nausea, vomiting, abdominal cramping, diarrhea, fever, headache, Diarrhea is more prevalent in adults, vomiting more common in children. | 12-60 hrs | Raw produce, contaminated drinking water, uncooked foods and cooked foods that are not reheated after contact with an infected food handler; shellfish from contaminated waters |

TABLE 2-continued

Exemplary Pathogenic Microorganisms Identified by Methods According to This Disclosure
Table 2

| Organism | Common Name of Illness | Onset Time After Ingesting | Signs & Symptoms | Duration of Illness | Food Sources |
|---|---|---|---|---|---|
| Salmonella | Salmonellosis | 6-48 hours | Diarrhea, fever, abdominal cramps, vomiting | 4-7 days | Eggs, poultry, meat, unpasteurized milk or juice, cheese, contaminated raw fruits and vegetables |
| Shigella | Shigellosis or Bacillary dysentery | 4-7 days | Abdominal cramps, fever, and diarrhea. Stools may contain blood and mucus. | 24-48 hrs | Raw produce, contaminated drinking water, uncooked foods and cooked foods that are not reheated after contact with an infected food handler |
| Staphylococcus aureus | Staphylococcal food poisoning | 1-6 hours | Sudden onset of severe nausea and vomiting. Abdominal cramps. Diarrhea and fever may be present. | 24-48 hours | Unrefrigerated or improperly refrigerated meats, potato and egg salads, cream pastries |
| Vibrio parahaemolyticus | V. parahaemolyticus infection | 4-96 hours | Watery (occasionally bloody) diarrhea, abdominal cramps, nausea, vomiting, fever | 2-5 days | Undercooked or raw seafood, such as shellfish |
| Vibrio vulnificus | V. vulnificus infection | 1-7 days | Vomiting, diarrhea, abdominal pain, blood borne infection. Fever, bleeding within the skin, ulcers requiring surgical removal. Can be fatal to persons with liver disease or weakened immune systems. | 2-8 days | Undercooked or raw seafood, such as shellfish (especially oysters) |

First, a database was constructed using data from approximately 35,000 food or environmental samples (of which about 10% contained traces of pathogenic microorganisms as shown in Table 3) using two components: microorganism presence and chemical composition. Pore sequencing in combination with use of characteristic polymorphic gene regions (comprising SNP's, RFLP's, STRs, VNTR's, hypervariable regions, minisatellites, dinucleotide repeats, trinucleotide repeats, tetranucleotide repeats, simple sequence repeats, indels, and insertion elements) associated with a wide diversity of microorganisms were used to analyze each sample for the presence or absence of 17,800 different bacterial species (representing both pathogenic and non-pathogenic bacterial species). Additionally, data on sample composition was collected for 4,600 food ingredients in each environmental/food sample.

The data using the top bacteria associated with pathogen contamination (exemplified in FIG. 5) was used to train a classification model, which was tested for overfitting by machine learning techniques.

We further tested the performance of the model by testing a set of unknown food or environmental samples (50% of each). The full results of and ROC analysis of accuracy and precision of the classification models are presented in Table 3. In the cases of all the pathogens in Table 3, the metagenomics-based classification model had higher than 95% precision and 97% accuracy for pathogen detection.

TABLE 3

Independent Validation of Pathogen Prediction in Unknown Samples
Table 3

| Pathogen | Accuracy Score | Precision Score |
|---|---|---|
| Vibrio parahaemolyticus | 99.78% | 96.55% |
| Staphylococcus aureus | 99.67% | 100.00% |
| Yersinia pseudotuberculosis | 99.45% | 100.00% |
| Vibrio vulnificus | 99.12% | 100.00% |
| Shigella boydii | 99.12% | 100.00% |

TABLE 3-continued

Independent Validation of Pathogen Prediction in Unknown Samples
Table 3

| Pathogen | Accuracy Score | Precision Score |
|---|---|---|
| Salmonella enterica | 96.16% | 94.39% |
| Escherichia coli | 97.48% | 98.40% |

Example 16

In Silico Evaluation of Primer Sensitivity and Specificity

This example describes the in silico evaluation of primer sensitivity and specificity for pathogen detection in PCR assays. First, a candidate primer pair was mapped against inclusion and exclusion sequences in sequence databases. Secondly, the identified hits are tabulated based on predicted amplification patterns in order to then determine the sensitivity and specificity of the primer pair in silico.

Figure 17:
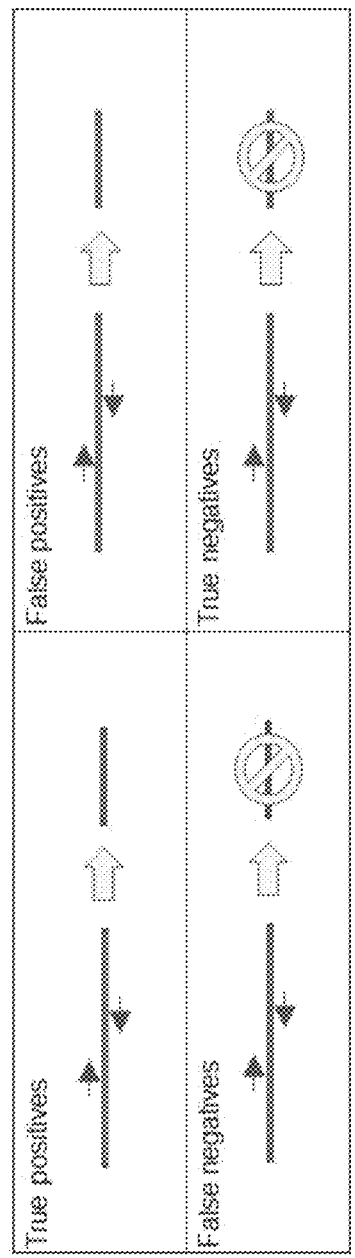
FIG. 17: illustrates the in silico prediction of primer sensitivity/specificity.

Specifically, a primer pair was designed to target *Salmonella* Montevideo and *Salmonella* Oranienburg. The composition of the sequence database for in silico evaluation contained 7705 *Salmonella* genomes, including 98 *Montevideo/Oranienburg* genomes, and 1707 non-*Salmonella* genomes (total of 9412 genomes). Tabulation of the analysis results showed that the exact number of 98 *Salmonella* Montevideo and Oranienburg genomes was identified as true positive hits. The remaining 9314 (which equals the total number of 9412 genomes minus the 98 true positive hits identified) genomes were characterized as true negative results. The results are shown in FIG. 17.

Example 17

Reuse of Flow Cells

This example shows that the MinION/GridION flow cell can be reused for sequence sample analysis for at least 2 times. Between each sample analysis (50 samples analyzed in each analysis) the flow cell was washed with a buffer system resulting in 30,000 reads and 26,000 reads per sample during the second and third reuse, respectively, compared to 36,000 reads per sample when using a new flow cell (FIG. 18). FIG. 19 illustrates that the number of reads per sample for reused MinION/GridION flow cells was well above the acceptable minimum threshold of 10,000 (10 K) reads per sample.

Example 19

Automated Pathogen Risk Detection

A significant source of confounding data in pathogen risk detection is contamination of samples by resident microorganisms on human handlers. Accordingly, we deployed a biomek-based sample sequencing platform that requires no human handling after enrichment (see FIG. 11 and FIG. 12) to implement the methods of Examples 10-13 and 15. Automation included every step of library preparation post incubation of the samples as in Examples 1-6, and included cell lysis, PCR, clean up, and sequencing. An automated handling system is illustrated in FIG. 11.

To determine the performance of our automated handling system, we analyzed samples spiked with 10 different *Salmonella* serotypes (*Enteritidis, Thyphimurium, I 4_[5]_12:i:-, Newport, Javiana, Infantis, Montevideo, Heidelberg, Muenchen*) by automated or manual handling. The results are presented in FIG. 20. Serotype detection accorded 100% between manual and automatic handling, and a student's T-test of the number of sequencing reads generated indicated no significant difference between manual and automated handling.

Example 20

Detection of Food Product Expiration/Shelf Life by Microbiome Metagenomics

A significant limitation of existing environmental pathogen detection methods is that they involve culturing, which involves the use of multiple different specialized media to detect different classes of pathogens (e.g. bacteria autotrophic for one or more nutrient vs those not). This severely limits the ability to detect food contamination during storage. Accordingly, we applied our environmental sampling/pore sequencing technique as outlined in Examples 1-13 on 100 samples of chicken wings and 100 samples of ground chicken. Each sample was analyzed for the presence/absence of 17,800 pathogenic and non-pathogenic bacteria.

Figure 21:
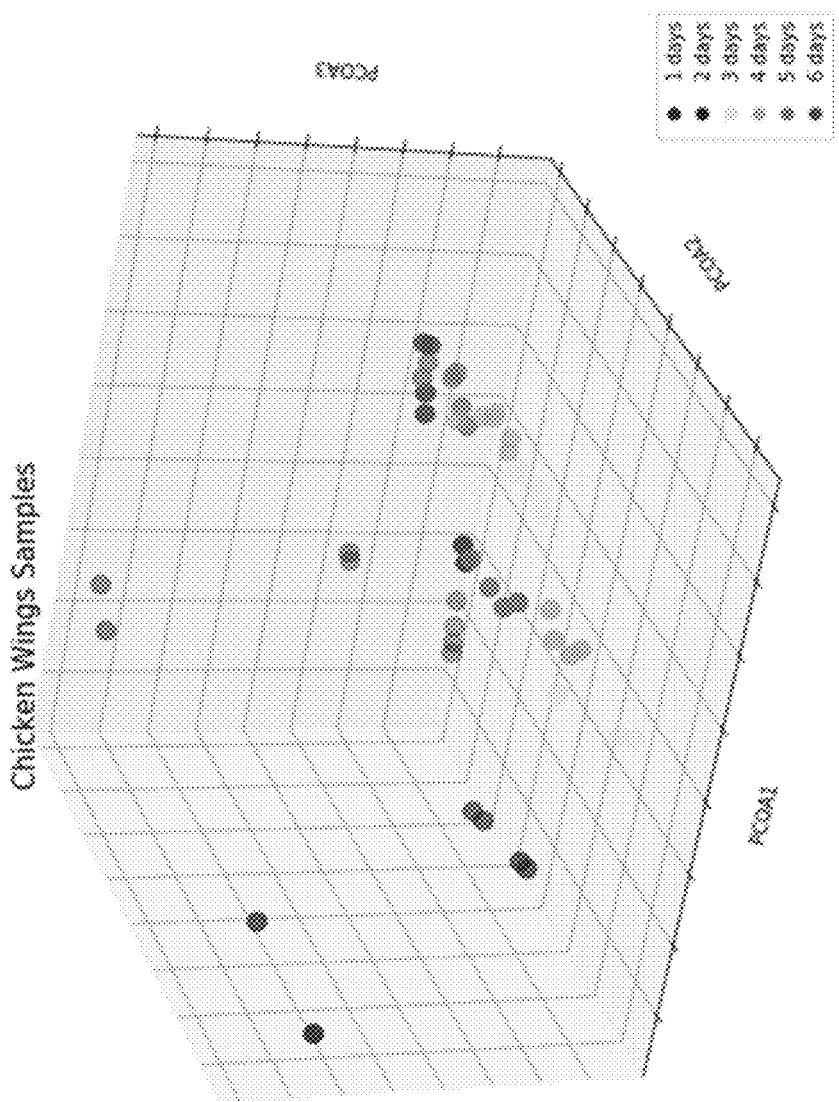
FIG. 21: illustrates a principal component analysis to chicken wing chicken data sets.
Figure 22:
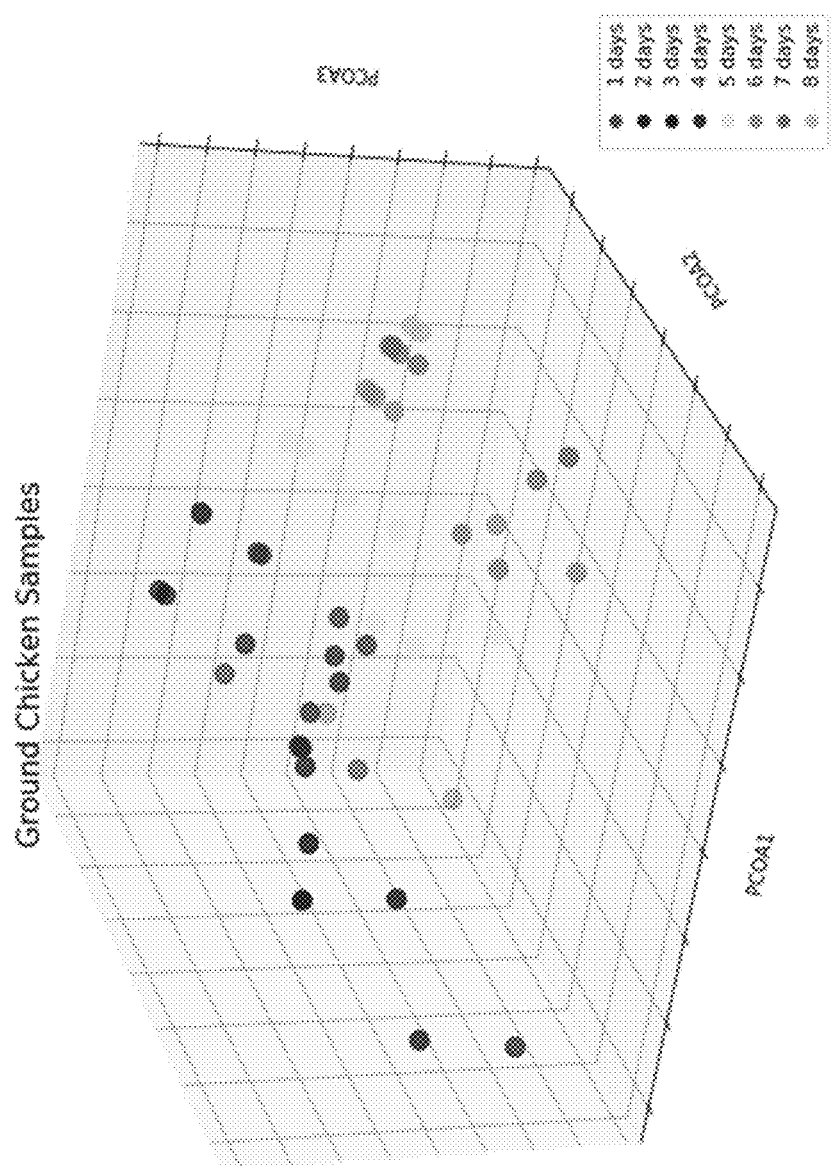
FIG. 22: illustrates a principal component analysis to ground chicken data sets.

We applied a principle components analysis to the whole or ground chicken data sets, which is presented in FIG. 21 and FIG. 22. Data points for both whole and ground chicken samples cluster along a discernable trajectory more than 2 days prior to their expiration date (see movement along PC2 in the whole chicken sample and PC1/PC3 in the ground chicken sample), while data points 1-2 days from expiration begin to rapidly diverge.

The principle components analysis suggested a classification model could be built to detect whether or not a whole or ground chicken sample had expired. The data on the presence/absence of 17,800 pathogenic and non-pathogenic bacteria was used to generate a classification model. When tested on an independent data set of samples, this classifier showed 97% accuracy in detecting samples past their expiration date using an ROC analysis.

Example 21

Comparison of Periodic and Nonperiodic Block Design for Sequencing Sample Barcodes; Reduction of Crosstalk Using Non-Periodic Block Primer Design To improve detection of desired sequences during sequencing runs, we tested the performance of different barcoding designs on sequence detection. We generated unique sequences of nucleotides with maximum Levenschtein distances and used them to generate two formats of barcodes to be applied to sequences during library preparation: a) a periodic block design, in which each barcode consisted of a unique block sequence repeated 3 times, and b) a nonperiodic block design, in which 3 unique blocks were combined in tandem for each barcode sequence.

Figure 23:
FIG. 23: illustrates periodic and nonperiodic barcode designs.
Figure 23:
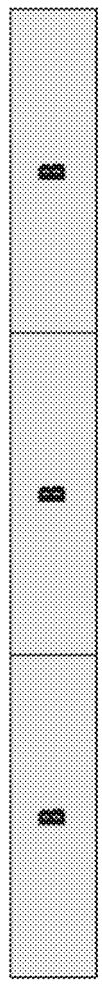
Figure 23:
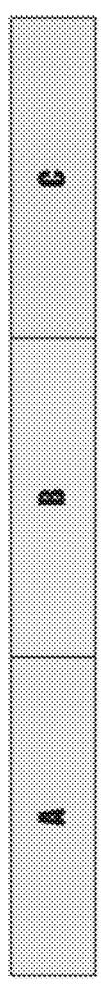

We tested these nonperiodic and periodic block designs alongside a conventional barcode design (which were designed barcodes provided by our sequencing platform provider) when applied to the same samples in test sequencing runs (see FIG. 23). Briefly, a defined Levenshtein distance between each "building block" or molecular index can be used to form larger barcodes. Such larger barcodes can have a period block design, such as barcodes created by repeating each block multiple times with the largest possible Levenshtein distance between the individual blocks (see FIG. 23). Alternatively, such barcodes can also have a nonperiod block design, such as barcodes created by concatenative multiple blocks that are unique to each barcode with the largest possible Levenshtein distance between the individual blocks (see FIG. 23).

We performed 10 ONT MinION runs and averaged the % of retained sequences and crosstalk for each run. The results are presented in Table 4. Both periodic and nonperiodic barcode designs showed improvements in retention and crosstalk versus the conventional design, with the nonperiodic design being the best in both metrics.

Both barcode designs present distinct advantages. Both increase the number of retained sequences and allow for adjustable precision by choosing 1, 2, or 3 blocks in demultiplexing, but the periodic design requires fewer repeat blocks and presents less complexity in demultiplexing, whereas the nonperiodic design allows for improved crosstalk prevention. The improved crosstalk prevention of the nonperiodic design suggests a method of reducing crosstalk during highly multiplexed runs or when a flowcell is reused.

TABLE 4

Performance of Conventional Barcode Design vs Periodic and Nonperiodic Block Designs
Table 4

|  | Conventional Design | Periodic Block Design | Nonperiodic Block Design |
| --- | --- | --- | --- |
| Retained Sequences | 85% | 96% | 98% |
| Crosstalk | 6% | 5% | 2% |

Example 22

Detection of Transient vs Resident Microbes by Metagenomics

Figure 24:
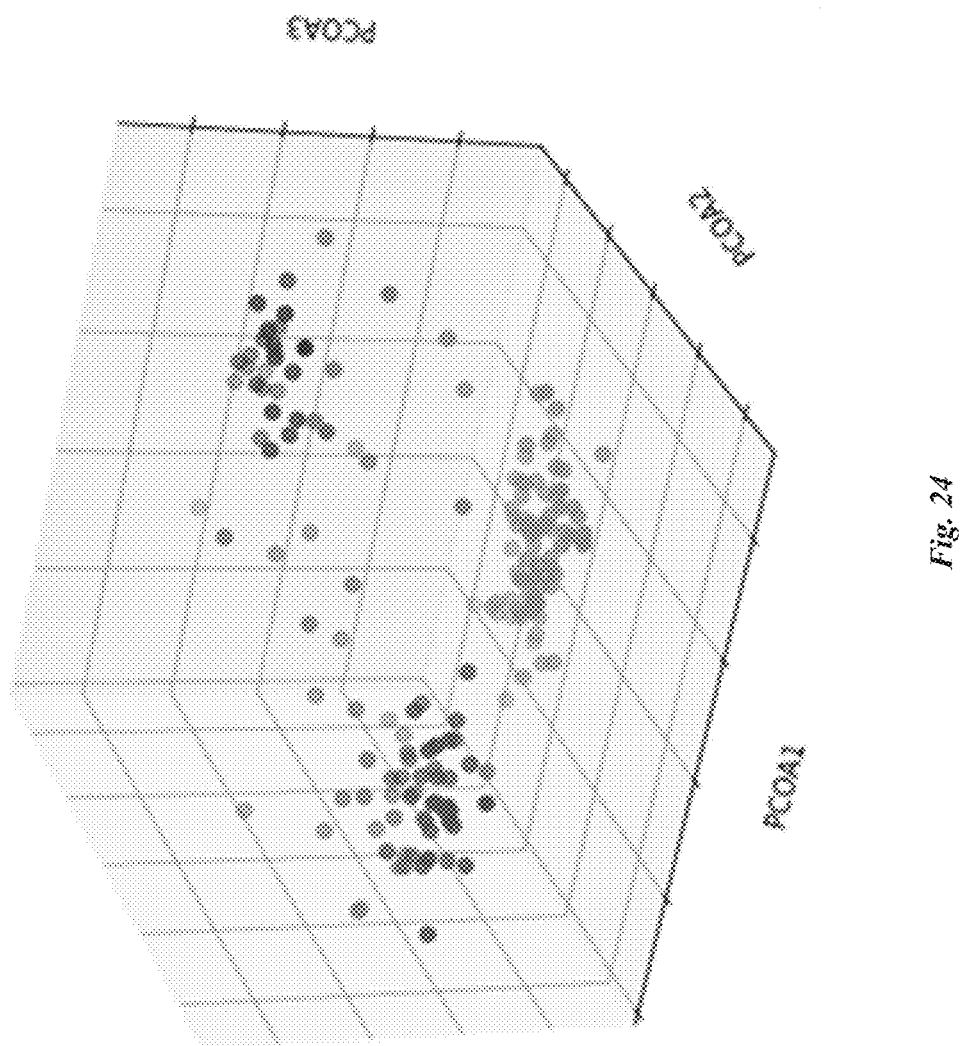
FIG. 24: illustrates a principle component analysis of *Listeria* sequences identifying clusters of closely related bacteria which likely originated from the same source.

*Listeria*-containing food and environmental samples were prepared, libraries were constructed, and sequencing was performed as in Examples 1-13 and 15. Samples were analyzed for the presence of *Listeria* by analyzing highly polymorphic genetic markers. A principle component analysis of the *Listeria* sequences isolated from sequencing (see FIG. 24) identified clusters of closely related bacteria which likely originated from the same source.

Example 23

Detection of Microbial Serotype Early in Sequencing Run

The length of time for a full sequencing run represents a major limitation in the speed of detection or serotyping of pathogenic bacterial strains by high-throughput sequencing. We hypothesized that using "live" detection calls during sequencing runs (which can be performed as early as 1 hour for ONT MinION and GridION, and 5 hours for Illumina MiSeq) would allow for certain bacteria to be detected/serotyped on a preliminary basis based on sequencing, with follow-up confirmation by other non-sequencing-based tests (e.g. Q-PCR).

We performed a test analysis of 50 environmental samples with about 15% positive for one of the pathogens identified in Table 3; positive samples were spiked with *Salmonella, Listeria, E. coli*, and *campylobacter* (2 samples each) from the top known pathogenic top strain/serotypes. Pathogen species was detected by detection of characteristic genomic markers. We compared the accuracy of species detection and serotyping at "live" and complete timepoints for the sequencing runs. The results are presented in Table 5. Early detection (1 hour for ONT MinION, and 5 hours for Illumina MiSeq) was 100% accurate for both formats, while MinION showed improved accuracy for serotyping.

TABLE 5

"Early call" Detection of Bacterial Species and Serotype
Table 5

| Platform | Sequences at early call | Detection calls | Serotyping calls | Final serotyping call |
| --- | --- | --- | --- | --- |
| MiSeq | 425,000 | 100% | 20% | 100% |
| MinION | 630,000 | 100% | 60% | 100% |

While preferred embodiments of the present invention have been shown and described herein, such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method comprising:
   (a) obtaining a first plurality of nucleic acid sequences from a first sample of a food processing facility, wherein said sample comprises a target nucleic acid comprising a periodic or a non-periodic barcode;
   (b) creating a data file in a computer that associates one or more of said first plurality of nucleic acid sequences with said food processing facility;
   (c) obtaining a second plurality of nucleic acid sequences from a second sample of said food processing facility, wherein said sample comprises a target nucleic acid comprising a periodic or a non-periodic barcode; and
   (d) scanning a plurality of sequences from said second plurality of nucleic acid sequences for one or more sequences associated with said food processing facility in (b).

2. The method of claim 1, wherein one or more of said first plurality of nucleic acid sequences associated with said food processing facility, one or more of said second plurality of nucleic acid sequences associated with said food processing facility, or both differentiates a transient pathogen from a resident pathogen.

3. The method of claim 1, wherein said data file associates a strain of said microorganism with said food processing facility.

4. The method of claim 1, wherein said first sample, said second sample, or both comprises a plurality of sequences from a plurality of microorganisms.

5. The method of claim 4, wherein at least one of said plurality of microorganisms is a non-pathogenic microorganism.

6. The method of claim 4, wherein at least one of said plurality of microorganisms is a pathogenic microorganism.

7. The method of claim 6, wherein said pathogenic microorganism is selected from the group consisting of a gram-negative bacterium, a gram-positive bacterium, a protozoon, a virus, and a fungus.

8. The method of claim 7, wherein said gram-negative bacterium is a *Salmonella* bacterium.

9. The method of claim 7, wherein said gram-negative bacterium is an *Escherichia* bacterium.

10. The method of claim 7, wherein said gram-positive bacterium is a *Listeria* bacterium.

11. The method of claim 7, wherein said gram-negative bacterium is a *Campylobacter* bacterium.

12. The method of claim 1, further comprising obtaining a third plurality of nucleic acid sequences from an third sample of said food processing facility.

13. The method of claim 1, wherein said first sample, said second sample, or both is a perishable.

14. The method of claim 13, wherein said perishable is a meat.

15. The method of claim 14, wherein said meat is a poultry, a red meat, a fish, or a swine.

16. The method of claim 13, wherein said perishable item is a fruit, an egg, a vegetable, a produce, or a legume.

17. The method of claim 1, wherein said first sample, said second sample, or both is a surface swab or a surface rinse of said environment.

18. The method of claim 1, wherein said first sample, said second sample, or both is a food storage container, a food handling equipment, or a piece of clothing from a worker of said environment associated with said food sample.

19. The method of claim 1, wherein said barcode is associated with said data file of (b), thereby associating said barcode with said food processing facility.

20. The method of claim 1, wherein obtaining said first plurality of nucleic acid sequences, said second plurality of nucleic acid sequences, or both comprises performing a sequencing reaction or a hybridization assay.

21. The method of claim 20, wherein said sequencing reaction is a pore sequencing reaction, a next generation sequencing reaction, a shotgun next generation sequencing, or Sanger sequencing.

22. The method of claim 20, wherein said sequencing reaction is a pore sequencing reaction.

23. The method of claim 22, wherein said pore sequencing reaction distinguishes an epigenetic pattern on a nucleic acid from said food sample or from said environmental sample.

24. The method of claim 23, wherein said epigenetic pattern is a methylation pattern.

* * * * *